United States Patent
Oberwager et al.

(10) Patent No.: US 6,510,430 B1
(45) Date of Patent: Jan. 21, 2003

(54) DIAGNOSIS AND INTERPRETATION METHODS AND APPARATUS FOR A PERSONAL NUTRITION PROGRAM

(75) Inventors: Bradford S. Oberwager, San Francisco, CA (US); Brian P. Moguin, Downingtown, PA (US)

(73) Assignee: Acumins, Inc., Philadelphia, PA (US)

( * ) Notice: Subject to any disclaimer, the term of this patent is extended or adjusted under 35 U.S.C. 154(b) by 0 days.

(21) Appl. No.: 09/256,946

(22) Filed: Feb. 24, 1999

(51) Int. Cl.$^7$ ............................................... G06F 17/30
(52) U.S. Cl. ..................... 707/10; 128/921; 600/300; 705/26; 707/102; 709/203; 709/219
(58) Field of Search ........................... 600/300; 705/26; 709/217, 218; 707/10; 128/921

(56) References Cited

U.S. PATENT DOCUMENTS

| | | | |
|---|---|---|---|
| 5,261,093 A | * 11/1993 | Asmuth | 707/2 |
| 5,654,011 A | 8/1997 | Jackson et al. | 424/635 |
| 5,686,429 A | 11/1997 | Lin et al. | 514/52 |
| 5,704,350 A | 1/1998 | Williams, III | 128/630 |
| 5,839,438 A | 11/1998 | Graettinger et al. | 600/300 |
| 5,948,061 A | * 9/1999 | Merriman et al. | 709/219 |
| 5,954,640 A | * 9/1999 | Szabo | 600/300 |

OTHER PUBLICATIONS

Kao, C. and Hwang, C.J. "A Dietary Recommendation Expert System Using OPSS", Proceedings of the Fall Joint Computer COnference, Oct. 25–29, 1987, pp. 658–663.*

Date, C.J. "An Introduction to Database Systems, vol. 1, Fourth Edition", Reading:Addison–Wesley, 1986, pp. 19–21, QA76.9.D3D37 1986.*

IEEE Intelligent Systems, Quicker, More Accurate Nutrition Plans for Newborn Infants (XP–002141553) Jan./Feb. 1998, pp. 65–69.

Basu, A; Hevner, A.R., Box Structured Development of Embedded Knowledge Based Systems: A Case Study (XP–02141554), 1991 IEEE, pp. 304–313.

Kao, Chiang; Hwang, C.J., A Dietary Recommendation Expert System Using OPSS (XP–000094226), 1987 IEEE, pp. 658–663.

* cited by examiner

Primary Examiner—Jean R. Homere
Assistant Examiner—Luke S Wassum
(74) Attorney, Agent, or Firm—Evelyn H. McConathy; Dilworth Paxson LLP

(57) ABSTRACT

The present invention relates to a method for developing an ingestible formula through a network that operates according to a hypertext transfer protocol (HTTP). A plurality of first statements inviting a plurality of first responses are received at a client computer system. The associated first responses are then received at the client computer system. A server computer system coupled over the network to the client computer system then receives the first responses. The server computer system processes the first responses according to a relational database to produce the ingestible formula. Various embodiments and features are disclosed.

23 Claims, 16 Drawing Sheets

Questionnaire—600

| Condition | Gender | STATEMENT SET—601 | |
|---|---|---|---|
| ADD | | Do you suffer from attention deficit disorder or the inability to concentrate? | 602 |
| Age 40 | m | Are you forty years of age or older? | 604 |
| Alcohol | | Do you consume more than two drinks of alcohol per day? | 606 |
| Anti-oxidant | | Do you desire increased anti-oxidant and anti-aging protection? | 608 |
| Anxiety | | Do you frequently feel anxious or suffer from anxiety? | 610 |
| Birth Control | f | Are you currently taking birth control pills? | 612 |
| Bones | | Do you have weak tooth enamel or bones? Many cavities or stress fractures? | 614 |
| Caffeine | | Do you consume more than two cups of caffeinated coffee or four caffeinated sodas per day? | 616 |
| Cancer | | Have your parents or siblings had cancer? | 618 |
| Cholesterol | | Do you have high cholesterol? | 620 |
| City | | Do you live or work in a city or greater metropolitan area? | 622 |
| Dieting | f | Are you currently dieting? (Consuming fewer than 1,600 calories per day.) | 624 |
| Dieting | m | Are you currently dieting? (Consuming fewer than 2,000 calories per day.) | 626 |
| Exercise | | Do you exercise intensely three or more times per week? | 628 |
| Glands | | Do you suffer from thyroid or other glandular dysfunction? | 630 |
| Hair | | Is your hair prematurely gray? Falling out? | 632 |
| Heart | | Are you concerned about cardiovascular disease or have you parents of siblings had heart disease? | 634 |
| Impotence | m | Are you concerned about impotence? | 636 |

FIG. 6-I

Questionnaire
STATEMENT SET

| Condition | Gender | |
|---|---|---|
| Infections | f | Do you get frequent sinus, yeast or other infections? |
| Infections | m | Do you get frequent sinus or other infections? |
| Memory | | Are you concerned about memory loss or Alzheimer's disease? |
| Milk | | Do you rarely drink milk or eat yogurt (less than 3 servings per week)? |
| Osteoporosis | | Do you want extra calcium (for osteoporosis protection) which is an additional pill added to your formula? |
| Perimenopausal | f | Are you experiencing perimenopausal symptoms (e.g., hot flashes, vaginal dryness or decreased libido?) |
| Perimenopausal | f | Are you perimenopausal? |
| PMS | f | Do you suffer from PMS? |
| Postadolescent | f | Are you postadoleescent but not yet perimenopausal? |
| Postmenopausal | f | Are you postmenopausal? |
| Pregnant | f | Are you pregnant or plan to be within two years? |
| Prostate | m | Do you have an enlarged prostate or prostate concerns? |
| Recovering | | Are you recovering from trauma, hospitalization or a degenerative disease including arthritis? |
| Sex | m | Do you wish to increase your sex drive? |
| Sight | | Do you suffer from night blindness? Any serious sight dysfunction? |
| Skin | | Is your skin blemished? Do you suffer from acne? |
| Smoke | | Do you smoke? |
| Stress | | Is your stress level high? Do you handle your stress poorly? |
| Sun | | Do you spend fewer than 15 minutes per day in direct sunlight? |
| Tendons | m | Do you have tissue or tendon injury? |
| Tired | | Do you frequently feel tired? |
| Veggies | | Do you eat fewer than three servings of vegetables per day? |
| Weight | | Would you like to reduce your weight? |

FIG. 6-2

ANTI-OXIDANT PACKAGE — 700

| Smoke (Rank: 10) | Heart/Cholesterol/Infection (Rank: 20) | Senior/Extra (Rank: 30) | Default (Rank: 40) |
|---|---|---|---|
| Vitamin A 5000.0 IU | Vitamin A 12500.0 IU | Vitamin A 10000.0 IU | Vitamin A 7500.0 IU |
| Beta Carotene 5000.0 IU | Beta Carotene 12500.0 IU | Beta Carotene 10000.0 IU | Beta Carotene 7500.0 IU |
| Vitamin C (base) 600.0 mg | Vitamin C (base) 280.0 mg | Vitamin C (base) 250.0 mg | Vitamin C (base) 260.0 mg |
| Vitamin E (base) 250.0 IU | Vitamin E (base) 300.0 IU | Vitamin E (base) 400.0 IU | Vitamin E (base) 225.0 IU |
| Condition: Smoke, Pregnant | Condition: Sight, Skin | Condition: Hair, Infections | Condition: |

B-Complex Package

| Baby (Rank: 10) | Heart/Cholesterol/Infection (Rack: 20) | Stress (Rank: 30) | Senior (Rank: 40) |
|---|---|---|---|
| Thiamine (B1) 5 mg | Thiamine (B1) 25 mg | Thiamine (B1) 30 mg | Thiamine (B1) 17 mg |
| Riboflavin (B2) 5 mg | Riboflavin (B2) 25 mg | Riboflavin (B2) 30 mg | Riboflavin (B2) 17 mg |
| Niacin (B3) 20 mg | Niacin (B3) 100 mg | Niacin (B3) 120 mg | Niacin (B3) 67 mg |
| Pantothenic Acid (B5) 10 mg | Pantothenic Acid (B5) 25 mg | Pantothenic Acid (B5) 30 mg | Pantothenic Acid (B5) 17 mg |
| B6 8 mg | B6 38 mg | B6 45 mg | B6 25 mg |
| B12 38 mcg | B12 188 mcg | B12 225 mcg | B12 126 mcg |
| Biotin 300 mcg | Biotin 375 mcg | Biotin 450 mcg | Biotin 350 mcg |
| Inositol 5 mg | Inositol 25 mg | Inositol 30 mg | Inositol 17 mg |
| Choline 5 mg | Choline 25 mg | Choline 30 mg | Choline 17 mg |
| Folic Acid 800.0 mcg | Folic Acid 850.0 mcg | Folic Acid 600.0 mcg | Folic Acid 800.0 mcg |
| Condition: Alcohol, BirthControl | Condition: Cholesterol | Condition: Caffeine, Anxiety | Condition: |

FIG. 7A-I

Cal/Mag/D Package

| High Risk (Rank: 10) | | Exercise/Women (Rank: 20) | | Senior (Rank: 30) | | Men (Rank: 40) | |
|---|---|---|---|---|---|---|---|
| Calcium (base) | | Calcium (base) | 300.0 mg | Calcium (base) | | Calcium (base) | |
| Magnesium | 275.0 mg | Magnesium | 100.0 mg | Magnesium | 325.0 mg | Magnesium | 200.0 mg |
| Potassium | 100.0 mg | Potassium | 125.0 mg | Potassium | 150.0 mg | Potassium | 100.0 mg |
| Vitamin D | 300.0 mg | Vitamin D | 400.0 mg | Vitamin D | 300.0 mg | Vitamin D | 200.0 mg |
| Vitamin K | 50.0 mg | Vitamin K | 20.0 mg | Vitamin K | 0.0 mg | Vitamin K | 30.0 mg |
| Condition: Bones | | Condition: Sun | | Condition: Only Women | | Condition: | |

Multi-Mineral

| High Risk (Rank: 10) | | Senior (Rank: 20) | | Men (Rank: 30) | | Woman (Rank: 40) | |
|---|---|---|---|---|---|---|---|
| Boron | 3.5 mg | Boron | 2.5999999 mg | Boron | 2.2 mg | Boron | 1.8 mg |
| Copper | 3.5 mg | Copper | 2.5999999 mg | Copper | 2.2 mg | Copper | 1.8 mg |
| Manganese | 35.0 mg | Manganese | 26.299999 mg | Manganese | 21.9 mg | Manganese | 17.5 mg |
| Molybdenum | 900.0 mcg | Molybdenum | 700.0 mcg | Molybdenum | 500.0 mcg | Molybdenum | 400.0 mcg |
| Zinc | 52.5 mg | Zinc | 39.400002 mg | Zinc | 32.799999 mg | Zinc | 26.299999 mg |
| Iron | 0.0 mg | Iron | 5.0 mg | Iron | 0.0 mg | Iron | 18.0 mg |
| Iodine | 200.0 mcg | Iodine | 125.0 mcg | Iodine | 100.0 mcg | Iodine | 150.0 mcg |
| Chromium | 175.0 mcg | Chromium | 125.0 mcg | Chromium | 200.0 mcg | Chromium | 150.0 mcg |
| Selenium | 250.0 mcg | Selenium | 150.0 mcg | Selenium | 200.0 mcg | Selenium | 150.0 mcg |
| Vanadium | 100.0 mcg | Vanadium | 25.0 mcg | Vanadium | 50.0 mcg | Vanadium | 50.0 mg |
| Amino | 200.0 mg | Amino | 200.0 mg | Amino | 200.0 mg | Amino | 200.0 mg |
| Condition: ADD | | Condition: Tendons, PMS | | Condition: Recovering,Sex,Glands,Perimenopausal | | Condition: | |

| Formula A 1 | Ingredient | Label | | Formula A 2 | Ingredient | Label |
|---|---|---|---|---|---|---|
| Pregnant | Vitamin A | 5000 IU | | Sight | Vitamin A | 12500 IU |
| Smoke | Beta-Carotene | 5000 IU (A) | | Sinus | Beta-Carotene | 12500 IU (A) |
| | Vitamin C | 600 mg | | | Vitamin C | 280 mg |
| | Vitamin E | 275 IU | | | Vitamin E | 300 IU |

| Formula B 1 | Ingredient | Label | | Formula B 2 | Ingredient | Label |
|---|---|---|---|---|---|---|
| Alcohol | Thiamin (B1) | 5 mg | | Cholesterol | Thiamin (B1) | 25 mg |
| Birth Control | Riboflavin (B2) | 5 mg | | | Riboflavin (B2) | 25 mg |
| | Niacin (B3) | 20 mg | | | Niacin (B3) | 100 mg |
| | Pantothenic Acid (B5) | 10 mg | | | Pantothenic Acid (B5) | 25 mg |
| | Pyridoxine (B6) | 8 mg | | | Pyridoxine (B6) | 38 mg |
| 756 | Cyanocobalamin (B12) | 38 mcg | | 757 | Cyanocobalamin (B12) | 188 mcg |
| | Biotin | 300 mcg | | | Biotin | 375 mcg |
| | Choline | 5 mg | | | Choline | 25 mg |
| | Folic Acid | 800 mcg | | | Folic Acid | 850 mcg |
| | Inositol | 5 mg | | | Inositol | 25 mg |

| Formula CMD 1 | Ingredient | Label | | Formula CMD 2 | Ingredient | Label |
|---|---|---|---|---|---|---|
| Bones | Calcium | 100 mg | | Sun | Calcium | 300 mg |
| 761 | Magnesium | 275 mg | | 762 | Magnesium | 100 mg |
| | Potassium | 99 mg | | | Potassium | 99 mg |
| | Vitamin D | 300 IU | | | Vitamin D | 400 IU |
| | Vitamin K | 50 mcg | | | Vitamin K | 20 mcg |

| Formula MM 1 | Ingredient | Label | | Formula MM 2 | Ingredient | Label |
|---|---|---|---|---|---|---|
| ADD | Boron | 4 mg | | PMS | Boron | 3 mg |
| | Chromium | 175 mcg | | Tendons | Chromium | 125 mcg |
| | Cooper | 4 mg | | | Cooper | 3 mg |
| | Iodine | 200 mcg | | | Iodine | 180 mcg |
| 766 | Iron | 0 mg | | 767 | Iron | 5 mg |
| | Manganese | 35 mg | | | Manganese | 26 mg |
| | Molybdenum | 875 mcg | | | Molybdenum | 656 mcg |
| | Selenium | 250 mcg | | | Selenium | 150 mcg |
| | Vanadium | 100 mcg | | | Vanadium | 25 mcg |
| | Zinc | 53 mg | | | Zinc | 39 mg |
| | Digezyme | 75 mg | | | Digezyme | 75 mg |
| | Protein Powder | 200 mg | | | Protein Powder | 200 mg |

FIG. 7B-2

| Formula A 3 | Ingredient | Label |
|---|---|---|
| Hair Infections f Infections m | Vitamin A<br>Beta-Carotene<br>Vitamin C<br>Vitamin E | 10000 IU<br>10000 IU (A)<br>250 mg<br>400 IU |

| Formula A 4 | Ingredient | Label |
|---|---|---|
| Default | Vitamin A<br>Beta-Carotene<br>Vitamin C<br>Vitamin E | 7500 IU<br>7500 IU (A)<br>350 mg<br>225 IU |

| Formula B 3 | Ingredient | Label |
|---|---|---|
| Anxiety<br>Caffeine<br><u>758</u> | Thiamin (B1)<br>Riboflavin (B2)<br>Niacin (B3)<br>Pantothenic Acid (B5)<br>Pyridoxine (B6)<br>Cyanocobalamin (B12)<br>Biotin<br>Choline<br>Folic Acid<br>Inositol | 30 mg<br>30 mg<br>120 mg<br>30 mg<br>45 mg<br>225 mcg<br>450 mg<br>30 mg<br>1000 mcg<br>30 mg |

| Formula B 4 | Ingredient | Label |
|---|---|---|
| Default<br><u>759</u> | Thiamin (B1)<br>Riboflavin (B2)<br>Niacin (B3)<br>Pantothenic Acid (B5)<br>Pyridoxine (B6)<br>Cyanocobalamin (B12)<br>Biotin<br>Choline<br>Folic Acid<br>Inositol | 17 mg<br>17 mg<br>67 mg<br>17 mg<br>25 mg<br>126 mcg<br>350 mcg<br>17 mg<br>800 mcg<br>17 mg |

| Formula CMD 3 | Ingredient | Label |
|---|---|---|
| Woman?<br><u>763</u> | Calcium<br>Magnesium<br>Potassium<br>Vitamin D<br>Vitamin K | 0 mg<br>225 mg<br>99 mg<br>300 IU<br>0 mcg |

| Formula CMD 4 | Ingredient | Label |
|---|---|---|
| Default<br><u>764</u> | Calcium<br>Magnesium<br>Potassium<br>Vitamin D<br>Vitamin K | 200 mg<br>200 mg<br>99 mg<br>200 IU<br>30 mcg |

| Formula MM 3 | Ingredient | Label |
|---|---|---|
| Glands<br>Perimenopausal<br>Perimenopausal<br>Sex<br>Recovering<br><u>768</u> | Boron<br>Chromium<br>Cooper<br>Iodine<br>Iron<br>Manganese<br>Molybdenum<br>Selenium<br>Vanadium<br>Zinc<br>Digezyme<br>Protein Powder | 2 mg<br>200 mcg<br>2 mg<br>100 mcg<br>0 mg<br>22 mg<br>547 mcg<br>200 mcg<br>50 mcg<br>33 mg<br>75 mg<br>200 mg |

| Formula MM 4 | Ingredient | Label |
|---|---|---|
| Default<br><u>769</u> | Boron<br>Chromium<br>Cooper<br>Iodine<br>Iron<br>Manganese<br>Molybdenum<br>Selenium<br>Vanadium<br>Zinc<br>Digezyme<br>Protein Powder | 2 mg<br>150 mcg<br>2 mg<br>150 mcg<br>18 mg<br>18 mg<br>438 mcg<br>150 mcg<br>50 mcg<br>26 mg<br>75 mg<br>200 mg |

| | Formula | Ingredient | Label |
|---|---|---|---|
| Anti-Oxident Protection | AO Anti-Oxidant, City | Co-Q10 Gingko Biloba Extract Grape Seed Extract | 15 mg 20 mg 50 mg |
| Arthro Care | AC | Glucosamine Sulfate Shark Cartilage | 500 mg 250 mg |
| Cardio-vascular care | CC Heart | Bioperine Co-Q10 Flaxseed Powder Ginger Extract Gugulipid Magnesium | 2 mg 15 mg 225 mg 25 mg 100 mg 50 mg |
| Cognitive Enhancement | CE Memory, ADD | Bacopin Bioperine Gingko Biloba Extract Siberian Ginseng Extract | 100 mg 2 mg 60 mg 50 mg |

| | Formula | Ingredient | Label |
|---|---|---|---|
| Extra Energy 795 | EE Tendons | Bee Pollen Siberian Ginseng Extract Spirulina Algae | 100 mg 100 mg 150 mg |
| Infection Protection 796 | IP Infections f Infections m | Bioperine Echinacea Extract Ginger Extract Spirulina Algae | 2 mg 100 mg 25 mg 150 mg |
| Prostate Protection 797 | PP Prostate | Bee Pollen Saw Palmetto Extract Selenium | 100 mg 250 mg 100 mcg |
| Weight Management 798 | WM Weight | Chromium Citrin Ginger Extract Spirulina Algae | 100 mcg 200 mg 25 mg 100 mg |

FIG. 7D

| To adjust an ingredient value, click on an up or down arrow. | | | | To add or remove a selection, highlight yes or no by clicking on the appropriate circular icon. | |
|---|---|---|---|---|---|
| Calcium 812 | 700 mg | ⇧ ⇩ | | Anti-oxident Protection<br>Co-Enzyme Q-10, Grape Seed Extract, Ginger Root Extract, Ginkgo Bilobe | ● yes  ○ no |
| Vitamin C 814 | 260 mg | ⇧ ⇩ | | | |
| Vitamin E | 225 IU | ⇧ ⇩ | | | |
| Vitamin A | 7500 IU | ⇧ ⇩ | | Weight Management<br>Citrin, Ginger Extract, Spriuline & Chromium Picolinate | ● yes  ○ no |
| Beta Carotene | 7500 IU | ⇧ ⇩ | | | |
| Thiamin (B1) | 5 mg | ⇧ ⇩ | | | |
| Riboflavin (B2) | 5 mg | ⇧ ⇩ | | Extra Energy<br>Siberian Ginseng, Bee Pollen, Magnesium Oxide & Blue Green Algae<br>Do not choose Extra Energy If you are allergic to pollen or bee stings. | ● yes  ○ no |
| Niacin (B3) | 20 mg | ⇧ ⇩ | | | |
| Pentothanic Acid (B5) | 10 mg | ⇧ ⇩ | | | |
| B6 | 8 mg | ⇧ ⇩ | | Cognitive Enhancement | ○ yes  ● no |
| B12 | 38 mcg | ⇧ ⇩ | | | |
| Biotin | 300 mcg | ⇧ ⇩ | | Cardiovascular Care | ○ yes  ● no |
| Inositol | 5 mg | ⇧ ⇩ | | Prostate Protection | ○ yes  ● no |
| Choline | 5 mg | ⇧ ⇩ | | Infection Protection | ○ yes  ● no |
| Vitamin D | 200 IU | ⇧ ⇩ | | Citrin | ○ yes  ● no |
| Folic Acid | 800 mcg | ⇧ ⇩ | | Ginkgo Biloba 24% | ○ yes  ● no |
| Magnesium | 200 mg | ⇧ ⇩ | | | |
| Potassium | 100 mg | ⇧ ⇩ | | Grape Seed Extract | ○ yes  ● no |
| Boron 848 | 2 mg | ⇧ ⇩ | | Saw Palmetto Extract 4:1 | ○ yes  ● no |
| Copper 850 | 2 mg | ⇧ ⇩ | | | |
| Manganese | 22 mg | ⇧ ⇩ | | Spiruline Algae | ○ yes  ● no |
| Molybdenum | 500 mcg | ⇧ ⇩ | | St. John's Wort | ○ yes  ● no |
| Zinc | 33 mg | ⇧ ⇩ | | | |
| Iodine | 100 mcg | ⇧ ⇩ | | ArthroCare | ○ yes  ● no |
| Chromium | 200 mcg | ⇧ ⇩ | | | |
| Selenium | 200 mcg | ⇧ ⇩ | | | |
| Venadium | 50 mcg | ⇧ ⇩ | | | |
| Vitamin K | 30 mg | ⇧ ⇩ | | | |
| Amino | 200 mg | ⇧ ⇩ | | | |

[ Order Online! ] ←-- To submit your order for processing, press the Order Online! button.

FIG. 8

DIAGNOSIS AND INTERPRETATION METHODS AND APPARATUS FOR A PERSONAL NUTRITION PROGRAM

BACKGROUND OF THE INVENTION

1. Field of the Invention

The present invention relates generally to a diagnosis and interpretation method for a personal nutrition program. More particularly, the present invention relates to an interactive, dynamic, Internet-based human-machine system with specialized problem-solving expertise that aids an individual consumer in developing a personal nutrition program tailored to the individual consumer's health needs and permits the consumer to produce individual products for ingestion.

2. Background Information

Being healthy means much more than getting treatment for an illness. Health-conscious individual consumers want to have more energy, be stronger, stay mentally alert, and feel healthier and happier; however, each of us is unique. No two bodies or lifestyles are identical. Some of us eat a well-balanced diet whereas others simply diet. One person's metabolism differs from another's. Our habits and programs differentiate us. Our genetic codes are individual. Where we live, what we do, the foods we eat, the air we breathe and the water we drink all combine to make each of us unique.

Studies prove that individual consumer diets do not contain the optimal levels of nutrition needed to prevent disease and attain peak health. For example, a 1978 study on consumption conducted by the National Food Council showed that not one person out of 21,500 surveyed received the entire Recommended Daily Allowance (RDA) of vitamins and minerals through diet alone. And, more than 80% of the men and 70% of the women received less than two-thirds of the RDA nutrients from their diets. Thus, consumers often need to supplement their diet in order to get the most out of life.

Many consumers have taken charge of their own health and wellbeing by taking daily nutritional supplements. To understand what products will benefit them and how to address their specific health issues, many consumers have turned to the Internet. The Internet is an international network of interconnected computers that enables millions of people to communicate with one another in "cyberspace" and to access vast amounts of information from around the world. This network of networks uses certain standard procedures for regulating data transmission between computers such as Transmission Control Protocol/Internet Protocol (TCP/IP) or HyperText Transfer Protocol (HTTP) for HyperText Markup Language (HTML) documents. The physical connections of the Internet and the protocols and communication procedures of the Internet are well-known to those in the art.

Through the Internet, individuals may seek out health and nutrition information to educate themselves about a healthier personal lifestyle and use this detailed information to make informed purchase decisions. However, even with the availability of this information through the Internet, it is very difficult for individual consumers to navigate through the myriad of health studies and decide what they should and should not consume. Furthermore, many consumers dismiss such important health information and resort to consuming eight, twelve, or even eighteen pills a day just to ensure that they are receiving sufficient amounts of vitamins, minerals, and anti-oxidants from generalized formula supplements made for the average person. Unfortunately, taking these generalized formula supplements made for the average person means ingesting binders, excessive fillers, and lubricants, as well as micronutrients in each menu of pills. Moreover, these various pills are often difficult to locate for purchase, are hard to swallow and may contain some vitamins or minerals that are not needed or may not have enough of what is needed. In turn, this leads many individuals to give up on their personal supplement program before the two or three months it takes for such programs to realize their full health potential.

Alternatively, individual consumers may obtain personalized nutritional supplements by seeking out expert nutritionists or pharmacists' services. FIG. 1 shows the various operations required in the prior art to distribute personalized supplements to an individual consumer. As shown in FIG. 1, the consumer first answers a series of health questions, as operation 12, on a form received from a nutrition consultant. The consumer then gives the answers to the nutritionist at operation 14. Upon receiving these answers, the nutritionist formulates a supplement program based on the consumer's answers by using public knowledge in operation 16 such as that found in published books. The nutritionist then tailors this formulation specifically to the individual consumer by using known, personal knowledge at operation 18 such as rules of thumb or heuristics. Heuristics enable the human expert to make educated guesses when necessary, to recognize promising approaches to problems and to deal effectively with erroneous or incomplete data. From operation 18, the nutritionist creates the supplement from raw powders in operation 20 and distributes the supplements to the consumer in operation 22.

The benefit of this process is that the consumer obtains a supplement that is personalized and free of extraneous material. However, this process is expensive for the consumer, is limited to geographic areas in which expert nutritionists reside, and requires the consumer to always consult the expert since the consumer lacks access to the expert's personal knowledge 18. The Internet is one area that provides a vehicle to address these problems.

As a unique and wholly new medium of worldwide human communication, the Internet is changing every area of humanity, primarily through the use of host computers. Host computers are those that store information and relay communications. Individuals can obtain access to the Internet from many different sources, generally hosts themselves or entities with a host affiliation. Many corporations provide their employees with access through an office network; most colleges and universities provide access for their students and faculty; many communities and local libraries provide free access; and an increasing number of storefront "computer coffee shops" provide access for a small hourly fee. Several major national "online services" such as America Online, CompuServe, the Microsoft Network and Prodigy offer access to their own extensive proprietary networks, as well as a link to the much larger resources of the Internet.

Anyone with access to the Internet may take advantage of a wide variety of communication and information retrieval methods. These methods are constantly evolving. Methods such as electronic mail ("e mail"), automatic mailing list services ("mail exploders," sometimes referred to as "listservs"), "newsgroups," "chat rooms," and the "World Wide Web" can be used to transmit text; most can transmit sound, pictures, and moving video images. Taken together, these tools constitute a unique medium—known to its users as "cyberspace"—located in no particular geographical location but available to anyone, anywhere in the world, with access to the Internet.

The best known category of communication over the Internet is the World Wide Web, which allows users to search for and retrieve information stored in remote computers, as well as, in some cases, to communicate back to designated sites. In concrete terms, the Web consists of a vast number of documents stored in different computers all over the world. Some of these documents are simply files containing information; however, more elaborate documents, commonly known as Web pages, are also prevalent. Each has its own address—rather like a telephone number. Web pages frequently contain information and sometimes allow the viewer to communicate with the page's (or "site's") author. They generally also contain "links" to other documents created by that site's author or to other (generally) related sites. Typically, the links are either blue or underlined text—sometimes images.

Navigating the Web is relatively straightforward. A user may either type the address of a known page or enter one or more keywords into a commercial "search engine" in an effort to locate sites on a subject of interest. A particular Web page may contain the information sought by the "surfer" or, through its links, it may be an avenue to other documents located anywhere on the Internet. Users generally explore a given Web page, or move to another, by clicking a computer "mouse" on one of the page's icons or links. Some "Web sites" provide information whereas other Web sites offer goods or services for purchase by credit card through online communication. Access to most Web pages is freely available, but some allow access only to those who have purchased the right from a commercial provider. The Web is thus comparable, from the user's viewpoint, to both a vast library including millions of readily available and indexed publications and a sprawling mall offering goods and services.

As noted, the power of the Internet goes far beyond delivering consumer information. From the sales of goods and services point of view, the Web constitutes a vast platform from which to market and sell to a worldwide audience of millions of buyers. Internet users may purchase goods or services, register their opinion on a variety of topics through online surveys, or manipulate game pieces in playing games against opponents thousands of miles away. All of these interactive actions may be performed from the comfort of the user's own home.

Taking advantage of the Internet, a fixed-form Excel spreadsheet Web page into which "Yes/No" answers are placed by consumers has been used in the eventual development of consumer supplement formulas. (Excel is a trademark of Microsoft Corporation of Redmond, Wash.) The consumer's answers are propagated through Excel spreadsheet cell formulas to yield a supplement formula. A nutritionist receives and reviews the supplement formula, alters the supplement formula, and sends it back to the consumer. After the consumer agrees to the formula, the nutritionist manufactures the supplement pills from raw powder.

This static structure system, although functional, is extremely difficult to maintain. For example, any changes to the makeup of the supplement formulas would require rewriting a significant portion of the spreadsheet and adding new formulas and questions to the system. Compounding this situation, the Web interface to this system makes use of the static Excel spreadsheet itself, launching a copy of Excel every time a formula is to be computed, and placing questionnaire answers into specific cells in the spreadsheet. Such an interface is both awkward and extremely inefficient. Moreover, the data used to support this system is not relational, does not permit for interactive modifications, and does not respond in real time.

Thus, even with the availability of these Internet-based, interactive actions, no Internet-based expert system exists that permits an individual to develop a personal nutrition program tailored to the individual consumer's needs, such that the resulting supplement formula is transmitted by the user directly to a manufacturing plant for the manufacture of the supplement product for shipment to the user.

What is needed is a human-machine system with specialized problem-solving expertise that permits individuals to personalize their choice of products for purchase through the Internet, where that system is linked directly to the product's manufacturing devices so that the process of selecting, altering, ordering, manufacturing, packaging and delivering the final product is streamlined and largely in the hands of the individual consumer.

What is also needed is a human-machine system with specialized problem-solving expertise that permits individuals to take charge of their personal health and nutrition through the Internet by assisting supplement consumers in developing personal nutrition programs designed specifically for their needs. The system should be dynamic enough to incorporate public and known information based on the latest knowledge that underlies human expertise with personal nutrition and nutrition products. Based on this expert information, the system should allow the consumer to obtain a specific program of recommended levels of the vitamins and minerals through easy-to-use, diagnostic questions. To benefit knowledgeable and experienced users of nutritional supplements, the system should further permit such users to personalize their nutrition program by adjusting the recommended levels of the nutrients in their program or by adding additional anti-oxidants or nutrients that work based on observational data of these nutrients. Through its interactive process and ability to dynamically change over time, the system should allow consumers to obtain a complete and balanced, high quality nutritional supplement program that cost effectively reduces the number of capsules a consumer needs to take, so as to increase purchasing convenience and program compliance.

SUMMARY OF THE INVENTION

The present invention relates to a method for developing an ingestible formula through a network that operates according to a hypertext transfer protocol (HTTP). A plurality of first statements inviting a plurality of first responses are received at a client computer system. The associated first responses are then received at the client computer system. A server computer system coupled over the network to the client computer system then receives the first responses. The server computer system processes the first responses according to a relational database to produce the ingestible formula. Various embodiments and features are disclosed.

BRIEF DESCRIPTION OF THE DRAWINGS

FIG. 6 shows a preferred embodiment questionnaire for operation 504 of the method of FIG. 5;

FIG. 7A shows a list of base ingredients arranged into the relational database of FIG. 2;

FIG. 7B exhibits alternate base supplement formulas within their own package in the relational database;

FIG. 7D shows a list of prodigies that may be arranged into the relational database;

FIG. 8 illustrates a Web page displaying ingredient values, alter features, optional nutrients, select features and a submit feature;

DETAILED DESCRIPTION OF THE INVENTION

Figure 1:
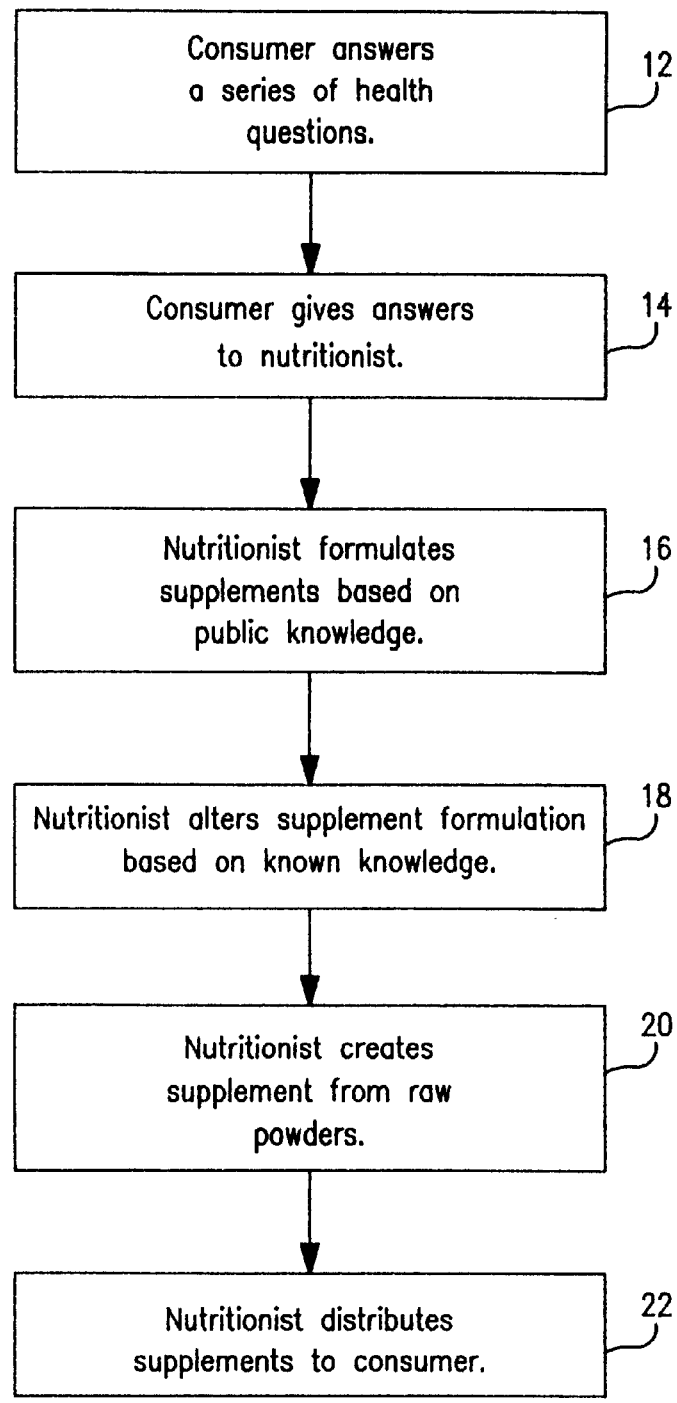
FIG. 1 shows the various operations required in the prior art to distribute personalized supplements to an individual consumer.

Referring to the figures, exemplary embodiments of the invention will now be described. The exemplary embodiments are provided to illustrate aspects of the invention and should not be construed as limiting the scope of the terms of the invention. The exemplary embodiments are primarily described with reference to block diagrams or flowcharts. As to the flowcharts, each block within the flowcharts represents both a method operation and an apparatus element for performing the method operation. Depending upon the implementation, the corresponding apparatus element may be configured in hardware, software, firmware or combinations thereof.

A portion of the disclosure of this patent document contains material which is subject to copyright protection. The copyright owner has no objection to the facsimile reproduction of the patent document or the patent disclosure by anyone, as the document appears in the Patent and Trademark Office patent file or records, but otherwise reserves all copyrights whatsoever. Copyright © 1999 GreenTree Nutrition, Inc.

Products produced by the process of the invention may contain vitamins, minerals, anti-oxidants, and prodigies. Vitamins may be organic compounds which our bodies require for normal functioning. As fat-soluble or water-soluble organic substances that are obtained naturally from plant and animal foods, vitamins are essential in minute amounts for normal growth and activity of the body, for vitality, and for general well-being. In addition, vitamins help to maintain normal appetite, digestion, mental alertness and our resistance to bacterial infections. Vitamins can slow or even reverse many health problems related to aging. with few exceptions, they are not created or synthesized by the body internally, but are found instead in natural foods and nutritional supplements.

Minerals such as calcium, iron, potassium, sodium, or zinc are as important as vitamins for our bodies to function properly. As an inorganic element that is essential to the nutrition of human beings, animals and plants, minerals may be naturally occurring elements that play a part in many of the biochemical and physiological processes necessary for good health. They are generally broken into two categories: essential minerals, which are required in our diets in amounts greater than one hundred milligrams per day, and trace minerals, which are required in amounts less than one hundred milligrams daily. The body itself cannot create minerals but obtains them from plant and animal foods, water or nutritional supplements.

Free radicals are unstable oxygen molecules which can cause cancer, disease, immune disorders and other potentially lethal illnesses. Anti-oxidants, such as vitamin E, vitamin C, and beta-carotene, have been shown in studies to reduce the risk from free radicals. Anti-oxidants may also improve the overall functioning of the body's immune system and delay the effects of aging. Since individual anti-oxidant nutrients differ in their transport through the body and therefore work best on different parts of the body, anti-oxidants are best taken in combination.

In this patent, the term "prodigy" or "prodigies" is used to describe those herbs, minerals and other nutrients which, since ancient times, have often been attributed near supernatural status because of their perceived healing and health-giving benefits. Until relatively recently, prodigies were either ignored or treated with great skepticism by scientifically trained nutrition experts and dieticians because prodigies lack clinical data. However, centuries of observational data, as well as modern research into their potential for increasing health and vitality, make prodigies an important part of a personal nutrition program. Prodigies may include bee pollen, Echinacea extract, flaxseed powder, gingko biloba extract, grape seed extract, shark cartilage, Siberian ginseng extract, and spirulina algae.

Figure 2:
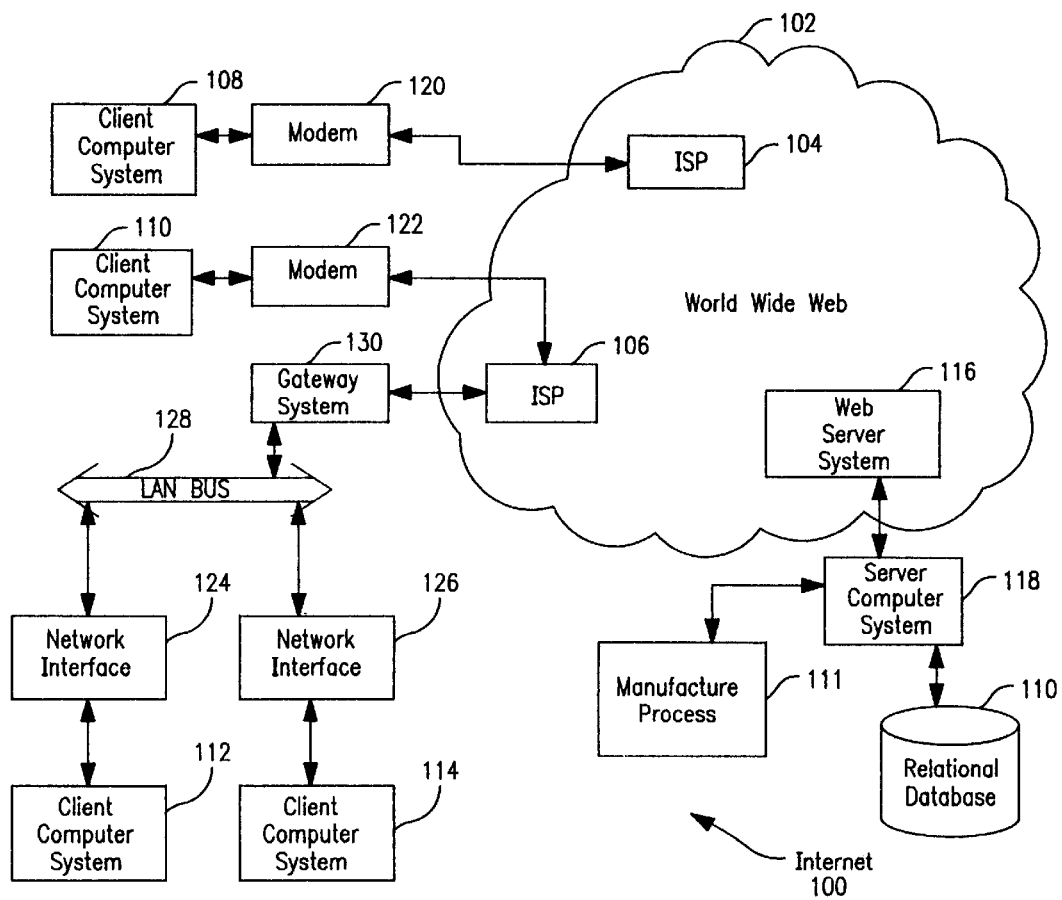
FIG. 2 shows the Internet with several client computer systems and a server computer system coupled to the World Wide Web according to one embodiment of the present invention.

FIG. 2 shows Internet 100 with several client computer systems 108, 110, 112, and 114 and server computer system 118 coupled to World Wide Web (WWW) 102 according to one embodiment of the present invention. Client access to World Wide Web 102 is typically provided by Internet Service Providers (ISP), such as ISP 104 and ISP 106. Users on client computer systems, such as clients 108, 110, 112, and 114, may be unrestricted public members and may obtain access to World Wide Web 102 through Internet Service Providers, such as ISP 104 and ISP 106. Access to World Wide Web 102 allows users of clients 108, 110, 112, and 114 to receive, view, and interact with Web pages. These Web pages are often provided by Web server systems, such as Web server system 116. Web server system 116 may be considered to be "on" World Wide Web 102. Often, these Web server systems are provided by the ISPs, such as ISP 104, although a computer system may be set up and connected to World Wide Web 102 as part of Internet 100 without that computer system being also an ISP. This is well-known in the art.

Web server system 116 is typically at least one computer system that operates as a server computer system and is configured to operate with the protocols of World Wide Web 102 as part of Internet 100. Optionally, Web server system 116 may be part of an ISP which provides access to World Wide Web 102 client systems. Web server system 116 is shown coupled to server computer system 118 which itself may be coupled to relational database 110 and manufacture process 111. Relational database 110 may embody public and known expert knowledge. For example, relational database 110 may embody nutrition or other knowledge as discussed in connection with FIGS. 7A, 7B, 7C, and 7D.

It will be appreciated that while two computer systems (116 and 118) are shown in FIG. 2, Web server system 116 and server computer system 118 may be one computer system having different software components providing the Web server functionality and the server functionality provided by server computer system 118. This will be described further below in connection with FIG. 3.

Internet symbiosis may be thought of as a close, prolonged association between two or more different Internet organisms of the same or different species that may, but does not necessarily, benefit each member. ISP 104 provides Internet symbiosis such as World Wide Web connectivity to the client computer system 108 through modem interface 120. Modem interface 120 may be considered separate or apart from client computer system 108. In a similar fashion, the ISP 106 provides Internet symbiosis for client computer systems 110, 112, and 114.

Although client computer systems 110, 112, and 114 may be in relationships of mutual benefit with or dependence upon World Wide Web 102 similar to client computer system 108, the connections are not the same for client computer systems 110, 112, and 114 as shown in FIG. 2. Client computer system 110 is coupled through modem interface 122 while client computer systems 112 and 114 are part of a Local Area Network (LAN) comprising network interfaces 124 and 126, LAN bus 128, and gateway computer system 130. Network interfaces 124 and 126 may be Ethernet network or other network interfaces. Client computer systems 112 and 114 are coupled to LAN bus 128 through network interfaces 124 and 126. To provide firewall and other Internet related services for the local area network, LAN bus 128 may be further coupled to gateway computer system 130. Gateway computer system 130, in turn, may be coupled to ISP 106 to provide Internet symbiosis to the client computer systems 112 and 114.

Client computer systems 108, 110, 112, and 114 may each view Web or HTML pages provided by the Web server system 116 when provided with the appropriate Web browsing software. These client computer systems may be a "WINTEL" computer system, a network computer, a Web TV system, or other computer systems. Moreover, gateway computer system 130 may be, for example, a conventional server computer system. Also, Web server system 116 may be a conventional server computer system. And, although FIG. 2 shows interfaces 120 and 122 as "modems," it will be appreciated that each of these interfaces may be an analog modem, Industry Standard Digital Network (ISDN) modem, cable modem, satellite transmission interface (for example, "Direct PC"), or other interfaces for coupling a computer system to other computer systems.

Figure 3:
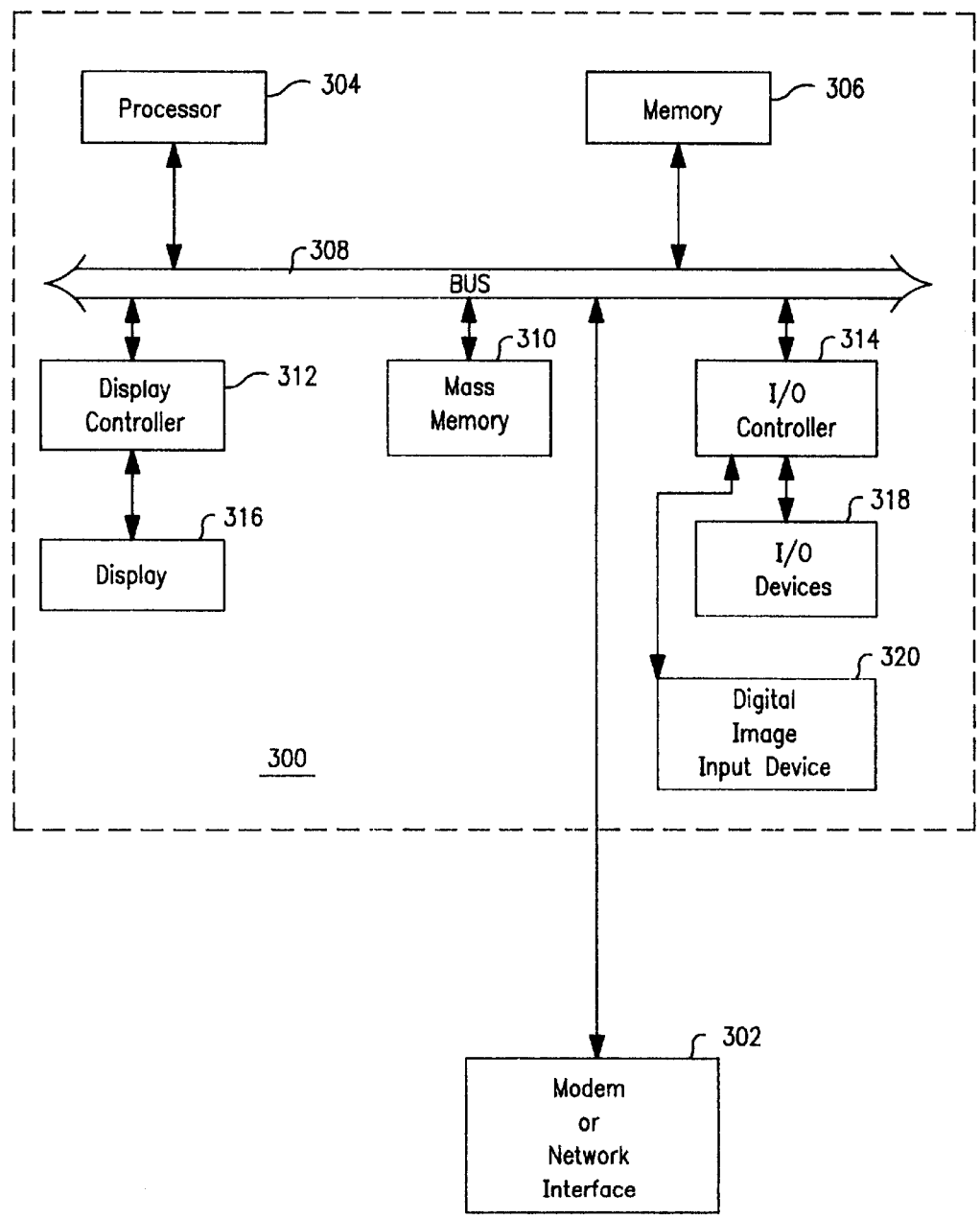
FIG. 3 shows one example of a conventional server computer system.

FIG. 3 shows one example of conventional server computer system 300. Computer system 300 may be used, for example, as client computer systems 108, 110, 112, and 114, Web server system 116, or server computer system 118 of FIG. 2. It will also be appreciated that such a computer system may be used to perform many of the functions of an Internet service provider, such as ISP 104 or ISP 106.

Computer system 300 may interface with external systems through the modem or network interface 302. Modem or network interface 302 may be considered to be part of computer system 300 and may be an analog modem, ISDN modem, cable modem, token ring interface, satellite transmission interface (for example, "Direct PC"), or other interfaces for coupling a computer system to other computer systems. Computer system 300 includes processor 304, which may be a conventional microprocessor such as an Intel Pentium microprocessor or Motorola Power PC microprocessor. Memory 306 is coupled to processor 304 through bus 308. Memory 306 may be dynamic random access memory (DRAM) and may also include static RAM (SRAM). Bus 308 also couples mass memory 310, display controller 312, and input/output (I/O) controller 314 to processor 304 and memory 306, as well as to each other.

Display controller 312 controls in the conventional manner a display on a display device 316. Display device 316 may be a cathode ray tube (CRT), liquid crystal display, or other display. The input/output (I/O) devices 318 is coupled to I/O controller. 314 and may include a keyboard, disk drives, printers, a scanner, and other input and output devices, including a mouse or other pointing device. Display controller 312 and I/O controller 314 may be implemented with conventional, well-known technology. Digital image input device 320 may be a digital camera coupled to I/O controller 314 to allow images from the digital camera to be input into computer system 300. Mass memory 310 is often a magnetic hard disk, an optical disk, or another form of storage for large amounts of data. Some of this data is often written into memory 306 by a direct memory access process during execution of software in computer system 300.

It will be appreciated that computer system 300 is one example of many possible computer systems that have different architectures. For example, WINTEL systems (systems that run a Microsoft Windows operating system on an Intel microprocessor) often have multiple buses, one of which may be considered to be a peripheral bus. Network computers may also be considered to be a computer system which may be used with the present invention. Network computers may not include a hard disk or other mass storage, and the executable programs are loaded from a network connection into memory 306 for execution by processor 304. A Web TV system, which is known in the art, may be considered to be a computer system according to the present invention, but it may not include certain features shown in FIG. 3, such as certain input or output devices.

A typical computer system will usually include at least a processor, memory, and a bus coupling the memory to the processor. Operating system software that controls computer system 300 may include a file management system, such as a disk operating system, which is part of the operating system software. One example of an operating system software with its associated file management system software is the operating system known as Windows '95 from Microsoft Corporation of Redmond, Washington, and its associated file management system, including Internet Explorer. The file management system is typically stored in mass memory 310 and causes processor 304 to execute the various operations required by the operating system to input and output data and to store data in memory, including storing files on mass memory 310.

Figure 4:
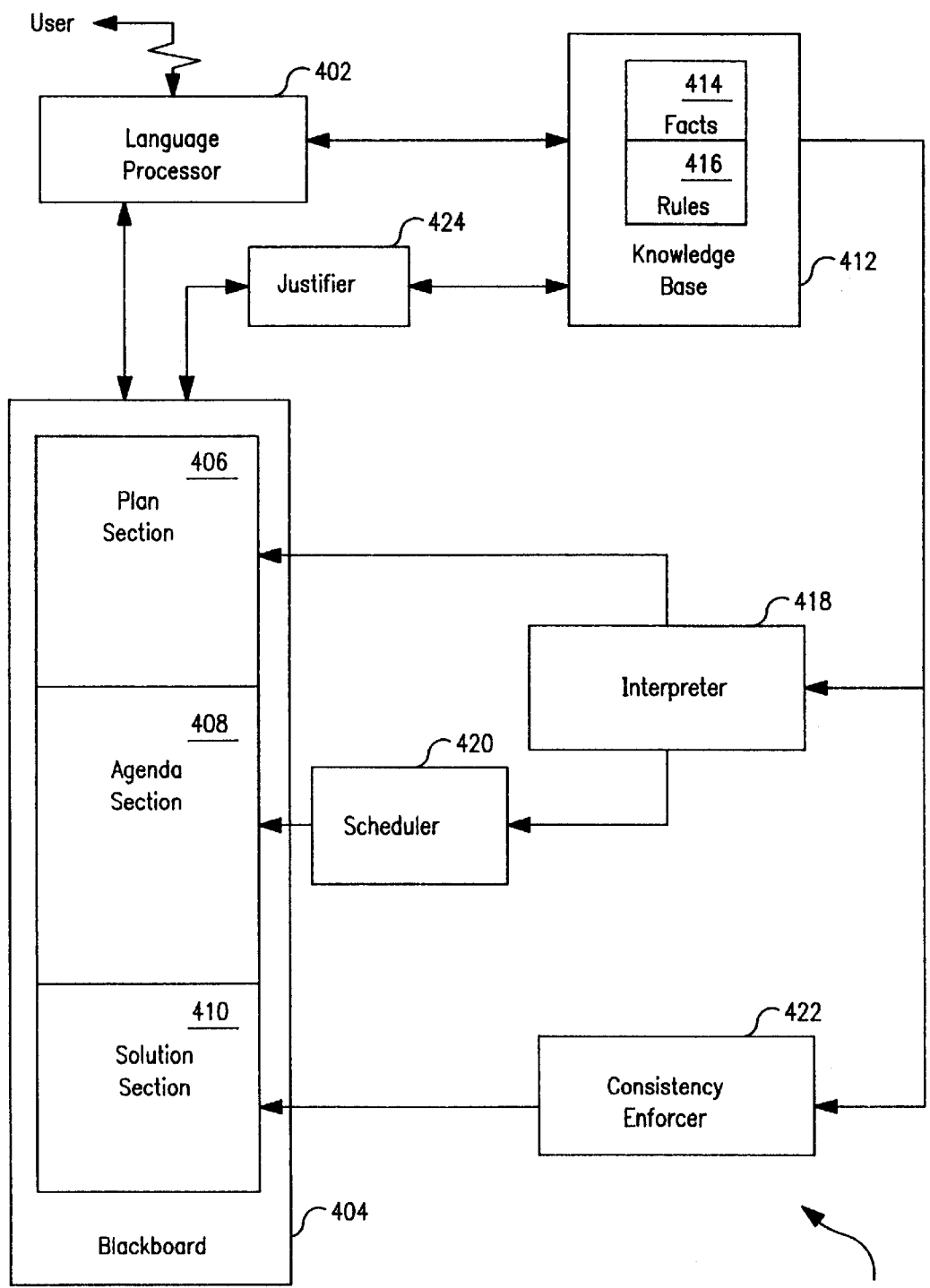
FIG. 4 illustrates one example of an expert system of the invention that may be implemented by known means within the hardware and software of the server computer system shown in FIG. 3.

FIG. 4 illustrates one example of an expert system of the invention that may be implemented by known means within the hardware and software of computer system 300 shown in FIG. 3. Expert system 400 may contain language processor 402 for problem-oriented communication between the user at client 108, 110, 112, or 114 of FIG. 2 and expert system 400. For example, language processor 402 may be a program that translates another program into a form acceptable by server computer system 300.

Coupled to language processor 402 may be blackboard 404. Blackboard 404 is used both to record intermediate and final results and work towards supplying the intermediate and final results to the user. Blackboard 404 may be divided into plan section 406, agenda section 408, and solution section 410. Each section addresses different results as discussed below.

Also coupled to language processor 402 may be knowledge base 412. Knowledge base 412 may comprise facts 414 plus heuristic planning and problem-solving rules 416. To apply facts 414 and rules 416, interpreter 418 is coupled to knowledge base 412. Interpreter 418 may be used to infer or otherwise predict the user's situation from a subjective or objective description provided by the user by comparing the description to preestablished criteria within knowledge base 412. Since the application of facts 414 or rules 416 typically require that they be applied in a particular order, scheduler 420 is coupled to interpreter 418 to control the order of rule processing. Where the application of facts 414 or rules 416 do not require that they be applied in a particular order, the output of interpreter 418 is directed to plan section 406. Otherwise, the output of interpreter 418 is directed to agenda section 408 of blackboard 404 through scheduler 420.

At times, data or knowledge may be supplied to or removed from expert system 400, either by the user through language processor 402 or by the system operator to within knowledge base 412. To account for this, consistency enforcer 422 may be coupled between knowledge base 412 and solution section 410 in order to adjust previously drawn conclusions when data or knowledge that alters the bases of support for these conclusions is added, removed, or otherwise changed. In order to help rationalize and explain the behavior of expert system 400, justifier 424 may be coupled between blackboard 404 at plan section 406 and knowledge base 412.

Although expert system 400 illustrates a preferred expert system of the present invention, all the elements described regarding expert system 400 may not be necessary for the implementation of an embodiment of the invention. For example, if facts 414 and rules 416 are prearranged in their particular order within knowledge base 412, scheduler 420 and agenda section 408 need not be included. If the responses supplied by the user are in a binary format such as a "yes" or a "no" response, language processor 402 may not be needed. One having ordinary skill in the art would recognize which elements of expert system 400 are necessary to implement a particular embodiment of the invention.

Figure 5:
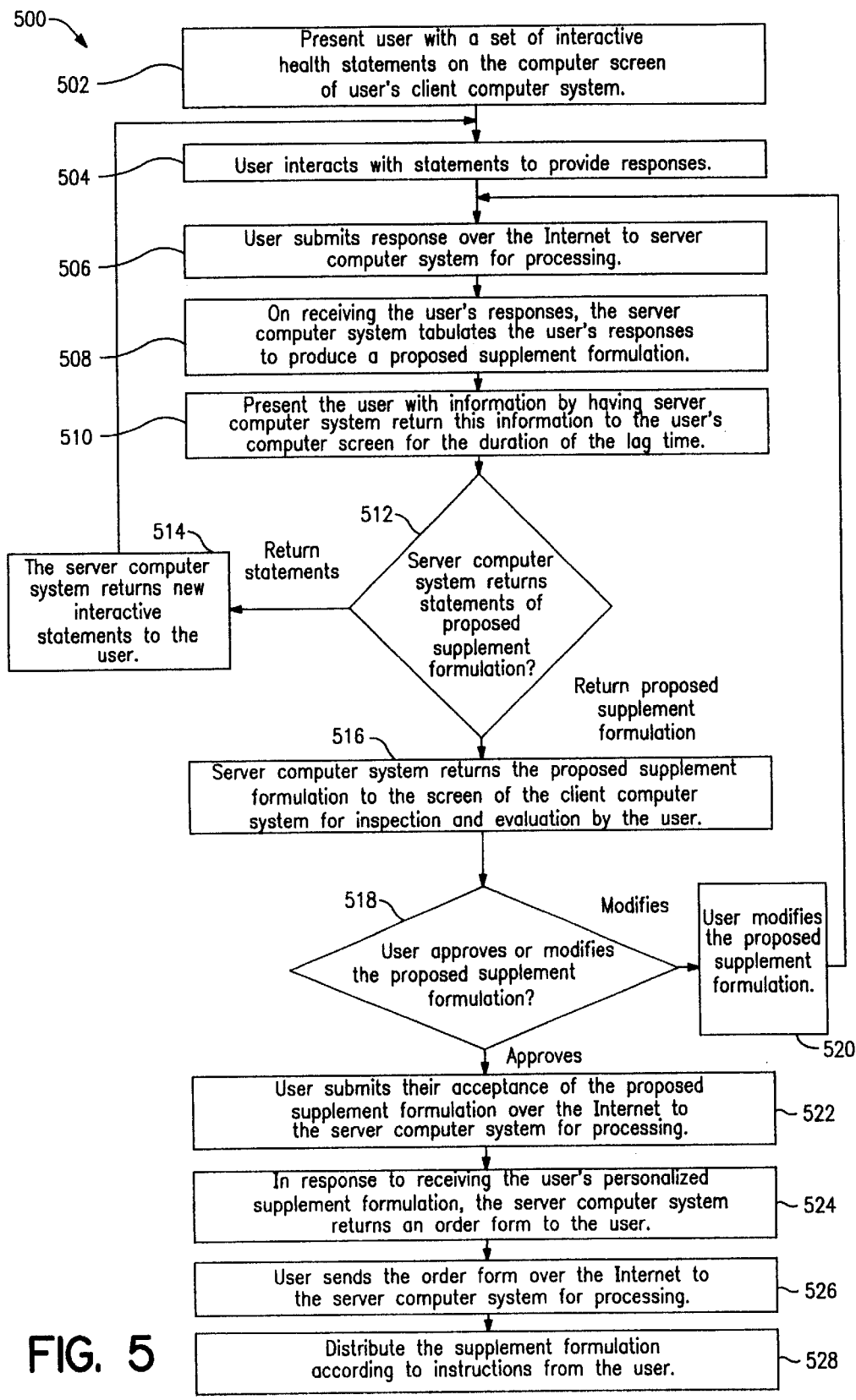
FIG. 5 is a flow diagram of the system process of the present invention.

FIG. 5 is a flow diagram of system process 500 of the present invention that may be implemented. The method of FIG. 5 begins in operation 502 where the user is presented with a set of interactive health statements on the computer screen of user's client computer system 108, 110, 112, or 114. The user may be presented with these statements in the form of a Web page where the user, for example, retrieves the Web page by either typing the address of the page or by entering one or more keywords into a commercial search engine in an effort to locate the page. The page may also be presented to the user as instigated by server 300 of FIG. 3 or brought to the attention of the user by a third party.

The statements of operation 502 are preferably in the form of questions, but may be in other forms that invite a response or action on the part of the user such as observations, remarks, comments, images, sounds, smells and the like. In operation 504, the user may interact with these statements by using the input devices of the client's computer system to provide responses. The statements presented to the user may, for example, request a yes/no binary response, request a numerical or keyword response, or permit arbitrary or discretionary responses based on, or subject to, individual judgment or preference. This is discussed below in connection with FIG. 6.

On completing their response to the presented statements, the user submits their response over the Internet to server computer system 300 for processing in operation 506. Server computer system 300 then tabulates the user's responses in operation 508 to produce a proposed supplement formulation. Preferably, server computer system 300 uses a relational database regarding tabulating the user's responses as discussed below in connection with FIGS. 7A, 7B, 7C, and 7D. The proposed supplement formulation may be any symbolic representation of a composition or of a composition and structure of a compound. The tabulation may be automatic.

In operation 512, server computer system 300 decides based on criteria in relational database 110 whether to return new interactive statements to the user or to return the proposed supplement formulation to the screen of the client computer system for inspection and evaluation by the user. If server computer system 300 decides the former, in operation 514, server computer system 300 may return new interactive statements to the user by returning to operation 502 and seeking further response from the user for processing. Relational database criteria that may prompt this is, for example, a "yes" response to the question "Are you taking any medication?" may return more specific statements to the user that request more specific information such as indicating the types of medication. If server computer system 300 decides the later, in operation 516, server computer system 300 returns the proposed supplement formulation to the screen of the client computer system for inspection and evaluation by the user.

Between operation 506 and operation 514 or between operation 506 and operation 516, there may be a lag time of approximately ten seconds. The invention takes advantage of this lag time to present the user, as a captive audience, with information such as an advertisement by having server computer system 300 return this information to the user's computer screen for the duration of the lag time as operation 510.

In operation 518, the user considers whether to approve the tabulation or to modify this proposed supplement formulation. If the user elects to modify the proposed supplement formulation, the user modifies the proposed supplement formulation at operation 520. This is discussed in more detail in connection with FIG. 8 below. From operation 520, the process returns to operation 506, where the user's modifications of the proposed supplement formulation are submitted to server computer system 300 for processing. If the user elects to accept the proposed supplement formulation, then the process continues from operation 518 to operation 522.

At operation 522, the user submits their acceptance of the proposed supplement formulation over Internet 100 of FIG. 2 to server computer system 300 for processing. In response to receiving the user's personalized supplement formulation, server computer system 300 may return an order form to the user as operation 524. In addition to conveying information, the order form may provide for user input such as the addition or deletion of products from the order, billing schedules for the order, or payment schemes. In operation 526, the user sends the order form over Internet 100 to server computer system 300 for processing. In operation 528, the supplement formulation comprising a personal nutrition program is distributed according to instructions from the user. These instructions may be provided on the order form or over the telephone, for example. The ordering, manufacturing, packaging and delivering the final product is discussed in connection with FIG. 9A and 9B below.

FIG. 6 shows a preferred embodiment questionnaire 600 for operation 504 of the method of FIG. 5. Questionnaire 600 may be any form, device, or item that contains a set of statements, especially general questions addressed to a statistically significant number of users as a way of gathering information. Questions 602 through 682 of statement set 601 may be derived from expert knowledge of lifestyle, health, and prevention issues in the area of nutrition and phrased in a way that invites a "yes" or "no" response. The response to each question may be preset to the answer "no" such that the user may change the response to "yes" by, for example, selecting the "yes" response on the Web page with a mouse pointer. Particular questions are gender specific as indicated in gender column 685. For example, question 612 relating to birth control pills is directed at females only since birth control pills are presently available only for females. These gender specific questions need only be presented to the appropriate gender and may be directed to that gender by having the user answer a question such as whether the user is male or female prior to answering statement set 601.

As can be seen, each question in statement set 601 is preferably associated with condition keywords 690. For example, question 620 "Do you have high cholesterol?" is assigned the condition keyword "cholesterol." A "yes" response would satisfy the condition so that the condition keyword "cholesterol" identifies one individual aspect of the user. The question could also be phrased so that a "no" response would satisfy the condition. Condition keywords 690 may be any device that represents something else by association, resemblance, or convention such as a printed word, symbol, or written sign.

The response to a statement within statement set 601 need not be a yes/no response. The statement may seek a numerical answer such as to cholesterol level, a keyword response such as high, average, or low cholesterol, or seek arbitrary responses based on, or subject to, individual judgment or preference, such as "I don't know if I have high cholesterol, but I have a coronary artery disease." Each of these styles of responses may be compared to a preestablished criteria within server computer system 300 such that server computer system 300 determines whether or not to identify the user's health with the condition keyword, here "cholesterol."

The actual text of statement set 601 that is displayed on the user's computer screen, for example, is independent of condition keywords 690, even though condition keywords 690 is associated with a user response that meets a certain preestablished criteria. This flexibility in presenting the user with various statements inviting response yields the capability of having different statements map to the same condition keyword. Thus, a user who responds "no" to question 620 "Do you have high cholesterol?" may meet preestablished criteria for high cholesterol by, for example, responding to second statement with a numerical answer that exceeds a certain cholesterol level threshold or responding to a third statement with a subjective description that is interpreted by server computer system 300 to meet the preestablished criteria for the "cholesterol" condition keyword 690, should more than one statement relating to cholesterol be presented to the user. The system is dynamic and may be easily changed. For example new statements, new condition keywords, different mapping routes between statements and condition keywords, and the like may each be added at will to the system.

Preferably, the proposed supplement formulation of operation 508 of FIG. 5 is a prescription of individual ingredients in fixed proportion. FIG. 7A shows a list of ingredients arranged into relational database 110 of FIG. 2 that may be used in the proposed supplement formulation. Relational database 110 may be comprised of base supplement formulation 700. Base supplement formulation 700 includes anti-oxidant package 710, B-complex package 720, Cal/Mag/D package 730, and multi-mineral package 740. Each of the four packages comprises four different supplement formulas for a total of sixteen supplement formulas within base supplement formulation 700. A particular ingredient may be contained within one or more supplement formulas and one or more packages.

Each supplement formula within a package receives a rank that distinguishes that supplement formula from the remaining supplement formulas in the package. Within a package having four supplement formulas, the supplement formulas may be ranked ten, twenty, thirty, or forty. For example, supplement formula 746 is within multi-mineral package 740 and has a rank of thirty as shown in FIG. 7A. Thus, in implementing the invention, each supplement formula may be identified from all other supplement formulas by its package and rank. Other techniques that uniquely identify each supplement formula may be used.

Each supplement formula shown in FIG. 7A, such as supplement formula 712, 718, 724, 732, 746, and 748, comprises a set of nutrients such as vitamins, minerals, or anti-oxidants that is preferably formulated based on expert knowledge. FIG. 7B exhibits alternate base supplement formulas 749 within each package 750, 755, 760, and 765. Alternate base supplement formulas 749 may be used within relational database 110.

Based on the responses received at server computer system 300 from the user, server computer system 300 returns the proposed supplement formulation to the screen of the client computer system in the form of a list of ingredient values that correspond to at least some of base supplement formulas 700. Preferably, one supplement formula is displayed from at least each of the four packages 710, 720, 730, and 740 of FIG. 7A. A proposed supplement formulation having less than one supplement formula from each of the four packages may also be displayed.

In is important to note that the database identified as relational database 110 is preferably a relational database that stores within it the relationships between the different ingredients based on knowledge of how the ingredients are interrelated as we have described here. For example, the interrelationship between boron, copper, and vitamin C has been described above. The database with its relational capabilities includes the relationships between ingredients, such as boron, copper, and vitamin C. Accordingly, when a user modifies a formulation in an interactive basis (for example, operation 520 in FIG. 5), the relational database takes into account the relationship between the ingredients and adjusts other ingredient values not adjusted by the user in order maintain those relationships.

Over the Internet, users on client computer system 108, 110, 112, and 114 of FIG. 2 may access relational database 110 of FIG. 2 in combination with server computer system 300 of FIG. 3 and expert system 400 of FIG. 4 to produce their own personalized proposed supplement formulation as discussed above in connection with operation 508 of FIG. 5 by employing condition keywords 690 of FIG. 6. As can be seen in FIG. 6, each question in statement set 601 is preferably associated with condition keywords 690. Moreover, each condition keyword 690 is associated with a particular supplement formula. For example, condition keyword 690 "cholesterol" is associated with question 620 of FIG. 6 and is associated with supplement formula 724 of FIG. 7A. Condition keywords 690 serve to link the user's response sent to server computer system 300 with the returned ingredients of the proposed supplement formulation from server computer system 300.

Supplement formulas such 714, 724, 732 and 746 of FIG. 7A have a precedence ranking system. Each of rank ten, twenty, thirty, and forty within packages 710, 720, 730, and 740 represents an order of precedence. Supplement formulas having lower rank are checked by server computer system 300 before higher ranking supplement formulas to see whether any of their conditions have been satisfied by any of the user's responses to statement set 601 of FIG. 6. Supplement formulas with no condition to satisfy are default supplement formulas and are chosen when no lower ranking formula's condition is met. For example, the conditions for supplement formula 722 of FIG. 7A are alcohol or birth control, the condition for supplement formula 724 is cholesterol, and the conditions for supplement formula 726 are caffeine or anxiety. Supplement formula 728 is the default supplement formula since supplement formula 728 is a supplement formula with no condition to satisfy. A user's response that satisfies the condition "alcohol" and the condition "anxiety" would be in line to receive supplement formula 726 since "anxiety" is the highest ranking condition satisfied.

Server computer system 300 uses relational database 110 to tabulate the user's responses through condition keywords 690. In regard to, for example, condition keywords 690 of B-complex package 720 and supplement formulas 722, 724, 726, and 728 of B-complex package 720, a user indicating on the Web page that they have high cholesterol in response to question 620 of FIG. 6, but indicating that they have low caffeine intake in response to question 616, and indicating that they do not suffer from anxiety in response to question 610, would be in line to receive supplement formula 724 of FIG. 7A. In this way, condition keywords 690 serve to bring relationship between the variety of human responses to statement set 601 of FIG. 6 and the associated ingredients within relational database 110 that would be recommended by an expert using both public and known knowledge.

It is important to note that the described ranking technique is but one example of selecting a supplement formula from a group of supplement formulas. Within the scope of the terms of the invention, any problem-solving technique in which the most appropriate solution of several found by alternative methods is selected at successive stages of a program for use in the next operation of the program is an acceptable technique for selecting a supplement formula from a group of supplement formulas.

Figure 7C:
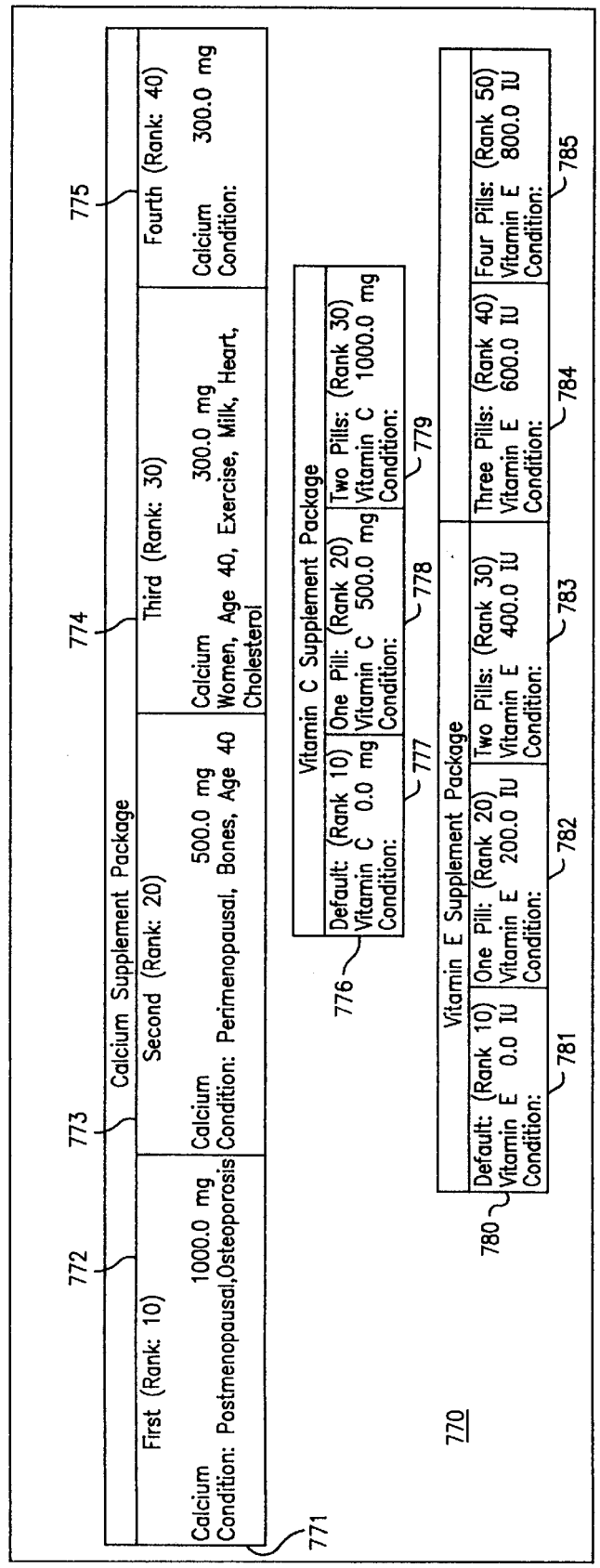
FIG. 7C shows a list of additional ingredients that may be arranged into the relational database.

Under an individual user's particular health circumstances, that individual may need additional nutrients beyond those specified within base supplement formulation 700 of FIG. 7A. These additional nutrients may include calcium, vitamin C, vitamin E, or prodigies. FIG. 7C shows a list of additional ingredients 770 that may be arranged into relational database 110. FIG. 7D shows a list of prodigies 790 that may be arranged into relational database 110.

An example of an individual who may need additional nutrients beyond those specified within base supplement formulation 700 would be a user with high cholesterol. The level of cholesterol in the bloodstream can influence the pathogenesis of certain conditions, such as the development of atherosclerotic plaque and coronary artery disease. High cholesterol is a typical problem experienced by men. Thus, a man with high cholesterol preferably receives extra calcium, for example, since the calcium mineral helps to maintain heart rhythm so as to better synthesize cholesterol through the liver.

A male user of the system who spends at least fifteen minutes in the sun as queried in statement 674 of FIG. 6 and does not have weak bones as inquired in statement 614 would receive 200.0 milligrams (mg) of calcium from supplement formula 738 of FIG. 7A since none of the conditions of Cal/Mag/D package 730 are satisfied and the default supplement formulation for Cal/Mag/D package 730 is supplement formula 738. A user of the system who indicates that they have high cholesterol in statement 620 of FIG. 6 may receive additional supplement formula 774 of FIG. 7C since condition keyword 690 "cholesterol" of calcium supplement package 771 is satisfied and is the highest ranked condition keyword 690 that is satisfied within calcium supplement package 771.

For server computer system 300 to return a proposed supplement formulation that includes additional calcium to a male user of the system who indicates that they have high cholesterol in statement 620 of FIG. 6, server computer system 300 may access the 200.0 mg value of calcium from base supplement formulation 738 of FIG. 7A and add it to the 300.0 mg value additional supplement formulation 774 of FIG. 7C for a total returned ingredient value of 500.0 mg calcium. In other words, such male user of the system who indicates in operation 504 of FIG. 5 that they have high cholesterol as sought by statement 620 of FIG. 6 would see the proposed ingredient value "calcium 500 mg" at their computer terminal screen in regards to the above example.

The Internet exists in no particular geographical location but is available to anyone, anywhere in the world, with access to the Internet. Thus, some Internet users of system process 500 of FIG. 5 will be more sophisticated regarding their own personal nutrition than the general population. It may be important, therefore, to present these users with optional nutrients such as vitamin C, vitamin E, or prodigies, beyond the base or base plus additional ingredient values returned to the user's computer terminal screen by server computer system 300. Optional packages may include vitamin C supplement package 776 and vitamin E supplement package 780 of FIG. 7C. Prodigy packages 790 of FIG. 7D may include anti-oxidant protection package 791, arthritis care package 792, cardiovascular care package 793, cognitive enhancement package 794, extra energy package 795, and weight management package 798. Some of these optional nutrients are displayed in FIG. 7C and FIG. 7D.

It is important to note that the distinction between base nutrients, additional nutrients, and optional nutrients resides within its placement within relational database 110. Expert knowledge is one of the factors that may be addressed in placing a nutrient within relational database 110. Thus, based on this factor or other factors, a base nutrient may be an additional or optional nutrient, an additional nutrient may be a base or optional nutrient, and an optional nutrient may be a base or additional nutrient. No restriction on a nutrient's classification are to be inferred from the nutrient terms used in the embodiments.

In operation 518 of FIG. 5, the user considers whether to approve the tabulation or to modify the proposed supplement formulation. If the user elects to modify the proposed supplement formulation, the user modifies the proposed supplement formulation at operation 520 of FIG. 5. FIG. 8 illustrates Web page 800 displaying ingredient values 802, alter features 804, optional nutrients 806, select features 808, and submit feature 810. Ingredient values 802 are those values within Web page 800 returned to the user's computer terminal screen by server computer system 300 after processing. Alter feature 804 may be up and down arrow icons that permit a user to increase or decease a particular ingredient value. Optional nutrients 806 are those nutrients outside of ingredient values 802 that sophisticated users may want to choose using select feature 802. Submit feature 810 permits the user to order the personalized vitamins, minerals, anti-oxidants, and prodigies developed by the user for the user's particular situation by sending the information to server computer system 300 after activation of submit feature 810. Each of these may be done in real time.

To modify a proposed ingredient value such as ingredient value 812 shown as calcium 700.0 mg in FIG. 8, the user selects one of the two arrow icons 813 associated with ingredient value 812 to increase or decrease ingredient value 812. Without restrictions such as expert advice that comes from public and known knowledge, a user could increase their personal calcium ingredient value to unhealthy or even toxic levels. For example, niacin (B3) in excess of 100.0 mg/day may cause skin irritation. Calcium in individual doses of over 2,000 mg/day may lead to hypercalcemia, constipation, and risk of urinary tract infection. Moreover, a user whose responses indicate a deficiency of, for example, calcium, should be restricted from decreasing calcium ingredient value 812 below levels that would be recommended by an expert. Thus, it is important to restrict the user's adjustments of individual ingredient values to those values between certain ranges for that individual ingredient.

Without restrictions, a user also could alter an individual ingredient value whose quantity is dependent upon quantities of one or more other ingredient values. For example, individual anti-oxidant nutrients, such as vitamin E, vitamin C, and beta-carotene, differ in their transport through the body and therefore work best on different parts of the body. Thus, anti-oxidants are best taken in combination. As another example, copper, which is essential for the utilization of vitamin C and is shown as ingredient value 850 in FIG. 8, affects the absorption of the mineral boron, ingredient value 848. If the amount of copper is increased, the amount of boron needs to be increased as well. In general, an increase in a first ingredient may inhibit body absorption of a second ingredient. The second ingredient value would have to be increased to account for the increase of the first ingredient. Thus, it is also important to restrict the range of the user's adjustments of individual ingredient values based on that individual ingredient's relationship with one or more ingredient values designed to be present in the final supplement formula. In other words, it will be appreciated by those in the art that restriction ranges maintained away from the unhealthy and toxic levels are to be effective given the interaction of one ingredient with the other ingredients that may be combined thereof.

In one embodiment of the invention, users are restricted to adjusting their personalized ingredient values 802 of FIG. 8 to those ingredient values that appear in base supplement formulations 700, as may be altered by additional ingredients 770 or prodigies 790. For example, a user may receive a calcium ingredient value of 700.0 mg. The 700.0 mg calcium value may be derived from the 200.0 mg calcium in base supplement formula 738 of FIG. 7A by adding the 500.0 mg calcium formula 773 of FIG. 7C. The user sees this 700.0 mg calcium as ingredient value 812 on Web page 800 of FIG. 8. A user depressing the up arrow icon 813 to increase calcium ingredient value 812 from 700.0 mg may be shown the value 1200.0 mg calcium. The 1200.0 mg calcium value is an increase of 1000.0 mg calcium over the 200.0 mg calcium in base supplement formula 738. The 1200.0 mg calcium may be derived from the 200.0 mg calcium in base supplement formula 738 of FIG. 7A added to the 1000 mg calcium formula 772 of FIG. 7C, such that the 1000 mg calcium formula 772 of FIG. 7C replaced the 500.0 mg calcium formula 773 of FIG. 7C in the summation. The presentation of the 1200 mg calcium value may also present the user the option to retain the 700.0 mg calcium value.

The process for decreasing the ingredient value is similar to the process for increasing the ingredient value. However, a user desiring to decrease the 700.0 mg calcium value may be prevented from decreasing the value since the analysis of the user's responses by server computer system 300 concluded that 700.0 mg calcium is the minimum amount of calcium needed by that particular user based on the user's unique responses. Under certain circumstances, such a restriction would work towards the health of the user.

There may be other reasons for conditioning the change of one ingredient value to the change of other ingredient values. Such reasons may include such as health, safety, general welfare, design, manufacturing, production, sales, convenience, or aesthetics. For example, it may be necessary to alter several ingredient values if the target ingredient value of change resides in a package having other ingredients. A user desiring to increase 2.0 mg copper ingredient value 850 shown in FIG. 8 may be presented with the 3.0 mg copper shown in supplement formula 767 of FIG. 7B and the 4.0 mg copper shown in supplement formula 766 of FIG. 7B. However, the user may also be presented with the changes to the other ingredient values as set out in supplement formula 767 or supplement formula 766. In this way, the user would be required to select between increasing their copper value and altering the other presented ingredient values or selecting to retain their original copper value. Note in FIG. 7B that as copper is increased, boron is increased by the same amount.

One aspect of the invention is that the products produced by the method of the invention may be personalized for the user of the system by the user of the system over, for example, the Internet, from anywhere in the world at any time of day or night. Preferably, the user personalizes their ingestibles over the Internet through their access to a server controlled by a business coupled to manufacturing equipment controlled by that business, where this equipment is subject to database constraints within the server, but otherwise may be at the disposal of and use by the individual Internet user. These database constraints, such as from knowledge that underlies human expertise reduced to computable, preestablished criteria forms, may be of public knowledge such as that found in books, such as text books and government publications, and personal knowledge, such as rules of thumb or heuristics.

Figure 9A:
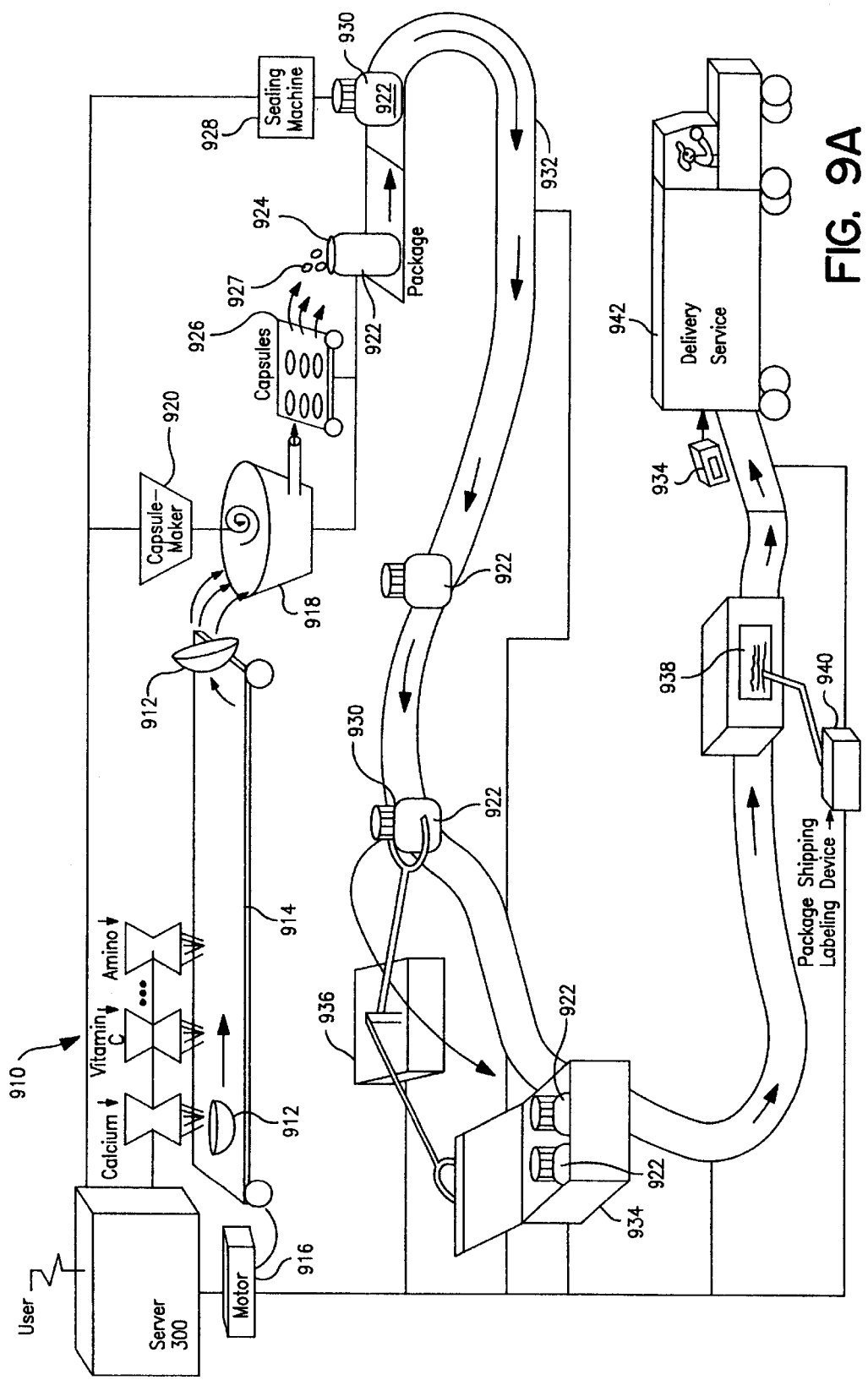
FIG. 9A illustrates a preferred method for receiving an order and manufacturing, packaging and delivering the final product.

FIG. 9A illustrates a preferred method for receiving an order and manufacturing, packaging and delivering the final product. From client computer system 108, 110, 112, or 114 of FIG. 2, the user may submit their personal nutrition program order over Internet 100 to server computer system 300 of FIG. 9A. On receipt of the order and receipt and verification of payment, server computer system 300 activates one or more of raw ingredient dispensers 910. There may be at least thirty three raw ingredient dispensers 910, each capable of dispensing at least one of the ingredients listed in Table I below. Other ingredients may be included, such as those manufactured under U.S. Pat. No. RE 33,988, U.S. Pat. Nos. 4,599,152, 4,698,360, 4,830,716, 4,863,898, or 5,536,506.

TABLE I

| Amino | Calcium (base) | Potassium |
| B1 (Thiamin) | Choline | Selenium |
| B2 (Riboflavin) | Chromium | Vanadium |
| B3 (Niacin) | Copper | Vitamin A |
| B5 (Pantothenic Acid) | Folic Acid | Vitamin C |
| B6 (Pyridoxine) | Inositol | Vitamin C (base) |
| B12 (Cyanocobalamin) | Iodine | Vitamin D |
| Beta Carotene | Iron | Vitamin E |
| Biotin | Magnesium | Vitamin E (base) |
| Boron | Manganese | Vitamin K |
| Calcium | Molybdenum | Zinc |

The activation signal from server computer system 300 causes raw ingredient dispensers 910 to release into container 912 their ingredients in the appropriate quantity such as those that might correspond to ingredient values 802. Conveyor 914 is controlled through motor 916 coupled to server computer system 300. Conveyor 914 passes container 912 each ingredient dispenser 910 and causes container 912 to transfer its contents into mixing vat 918.

Within mixing vat 918, the ingredients are engaged by capsule maker 920 as controlled by server computer system 300. Capsule maker 920 processes the ingredients and forms the ingredients into capsules 922. Each capsule 922 comprises the ingredients as specified by the user to server computer system 300. Capsules 922 may be any small soluble container made of gelatin that encloses a dose of mixed ingredients, may be any small, coated pellet or tablet taken by swallowing whole or by chewing, or any other appropriate mechanism that may be taken into the body by the mouth for digestion or absorption.

From mixing vat 918, at least one of capsules 922 is transferred into container 924 by tray device 926 as coupled to server computer system 300. Each container 924 is sealed at sealing machine 928 to form sealed container 930 and transported along conveyer 932. Conveyer 932 is coupled to motor 916. Both sealing machine 928 and conveyer 932 are controlled through server computer system 300.

As each sealed container 930 moves along conveyer 932, it is packaged into shipping box 934 by packaging machine 936. Shipping box 934 receives a mailing label 938 from package shipping label device 940. Packaging machine 936 and package shipping label device 940 are controlled by server computer system 300 and package shipping label device 940 receives the addressing information from the user through server computer system 300. Conveyer 932 then loads shipping box 934 onto delivery device 942. Delivery device 942 may be a truck, airplane, boat, or other device that may be operated manually or automatically.

The advantage of the method of FIG. 9A is that a single supplement may be manufactured largely through the control of the individual user. However, such a method requires large scale economics to be efficient. For smaller scale operations, it is preferred to premanufacture an array of supplements that embody all the permutations of ingredient values, optional formulas, and prodigies offered to the user.

Figure 9B:
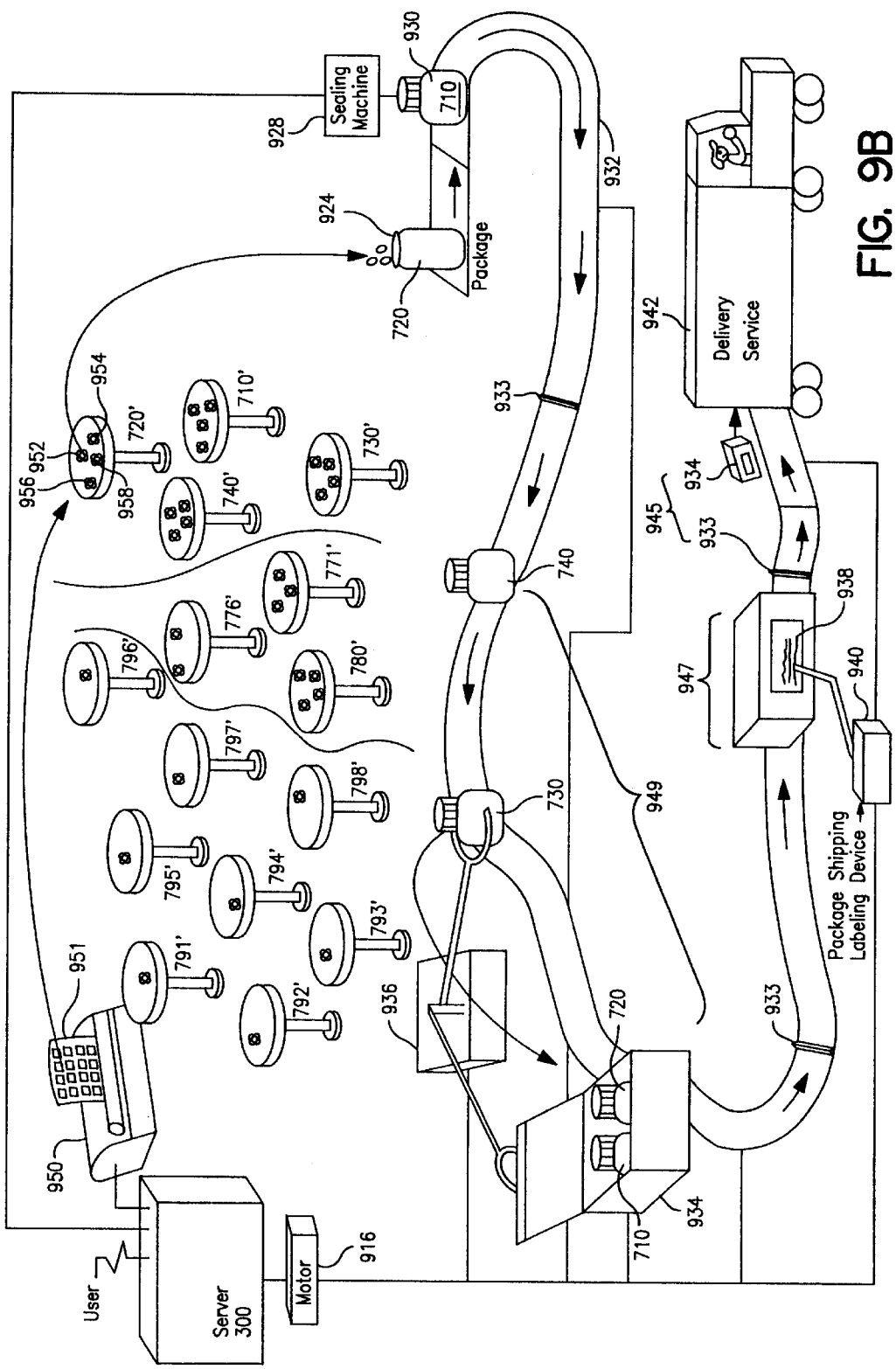
FIG. 9B illustrates an alternate embodiment of a preferred method for receiving an order and manufacturing, packaging and delivering the final product.

FIG. 9B illustrates an alternate embodiment of a preferred method for receiving an order and manufacturing, packaging and delivering the final product. Shown in FIG. 9B are an array of fifteen tables. Each table is for illustrative purpose, not utilitarian purpose, and represents one of the fifteen possible supplements that a user may purchase. The supplements located on these fifteen tables are premanufactured from, for example, the supplement formulas arranged within the fifteen packages disclosed in FIGS. 7A, 7C, and 7D. For example, located on table 720' are supplements 952, 954, 956, and 958. The formulation for supplement 952 is derived from supplement formula 722 of B-complex package 720 of FIG. 7A. Similarly, the formulation for supplement 954 is derived from supplement formula 724, supplement 956 is derived from supplement formula 726, and supplement 958 is derived from supplement formula 728.

From client computer system 108, 110, 112, or 114 of FIG. 2, the user may submit their personal nutrition program order over Internet 100 to server computer system 300 of FIG. 9B. Device 950 is coupled to server computer system 300 and prints out order 951. On reading order 951, a worker gathers a plurality of the appropriate supplement from, for example, table 720' and places these supplements into container 924. In this example, order 951 indicated that the user had requested supplement 952. The worker takes, for example, ninety pills of supplement 952 and places them in container 924.

Each container 924 is sealed at sealing machine 928 to form sealed container 930 and transported along conveyer 932. Conveyer 932 is coupled to motor 916. Both sealing machine 928 and conveyer 932 are controlled through server computer system 300.

Individual customer orders are separated by, for example, block 933. Block 933 may be any device that is capable of drawing distinction between each order. Shown in FIG. 9B are four different orders at different stages of the process. Order 951 is being placed into containers 924, where container 924 is then sealed by sealing machine 928. Order 949 is being transported along conveyer 932 for packaging into shipping box 934. Order 947 receives a mailing label 938 from package shipping label device 940. Packaging machine 936 and package shipping label device 940 are controlled by server computer system 300 and package shipping label device 940 receives the addressing information from the user through server computer system 300. Order 945 is loaded onto delivery device 942 by conveyer 932. The method of FIG. 9B may be further automated by having a machine read each order, select the appropriate supplement from the appropriated table, and place these supplements in its appropriate container.

Alternatively for the methods of FIG. 9B, each set of capsules that comprise a daily dose of nutrients for the user may be packaged into its own daily packet. A daily packet may be at least one sheet of food grade paper adhered together to form a sealed, open space into which one or more capsules may be stored. For instance, in a preferred, but non-limiting embodiment, a single capsule is packaged in each sealed paper; while in another, four capsules are packaged within the sealed packet. The disclosed number of capsules in each packet is intended to be exemplary, rather than limiting. A daily packet may also be a perforated sheet of plastic into which, one or more depressions are formed. A daily set of capsules, which as disclosed above may be of any selected number, but which is exemplified as one to a packet or four to a packet, may be stored into the one or more depressions, preferably one capsule per depression, and covered with a sealing sheet. A daily set of capsules, which as disclosed above may be of any selected number, but which is exemplified as one to a packet or four to a packet, may also reside on a wafer surface and is covered with a sealing sheet. The wafer surface and sealing sheet are preferably made from clear plastic. The daily packet conveniently permits the user to open for consumption one packet per day. As previously noted, each daily set of capsules may contain more or less than four capsules, and four is merely used to exemplify one preferred embodiment of the invention in which the daily regimen for an exemplary user is four capsules. The packets themselves may be stored in a larger container, such as a container storing a month's supply of thirty daily packets.

The products produced by the processes of the invention are not limited to vitamin or mineral supplements. Products over which the user controls the manufacture through the Internet and are to be taken into the body by the mouth for digestion or absorption are within the scope of the terms of the invention. The ingestible formulas for these products may be of materials, usually of plant or animal origin, that contain or consist of essential body nutrients, such as carbohydrates, fats, proteins, vitamins, or minerals, and are ingested and assimilated by an organism to produce energy, stimulate growth, and maintain life. Such products may include, but are not limited to, supplements, over-the-counter and prescription drugs, liquids, and foods that undergo application of heat especially for the purpose of later ingestion.

Among the benefits derived from the invention are the reduction and elimination of multiple jars of capsules and pills, and the minimization of confusion about which supplements to take along when traveling. The nutritional supplements may be produced in easy to swallow capsules that permit a user to reduce their daily intake of capsules and pills by 50% or more.

The exemplary embodiments described herein are provided merely to illustrate the principles of the invention and should not be construed as limiting the scope of the terms of the invention. Rather, the principles of the invention may be applied toward a wide range of systems to achieve the advantages described herein and to achieve other advantages or to satisfy other objectives, as well.

What is claimed is:

1. An interactive method for formulating through a network, a unique ingestible nutritional supplement, not a model, for an individual, the method comprising:

receiving a plurality of first statements inviting a plurality of first responses at a client computer system;

receiving the plurality of first responses at the client computer system;

receiving the plurality of first responses at a server computer system coupled over the network to the client computer system;

processing the plurality of first responses at the server computer system including an additional invitation for an additional response to supply data into a relational database to produce a unique formula for the ingestible supplement;

customizing the unique formula to the individual client by repeating the following steps as often as needed to meet the client's needs, comprising:

returning the formula for the ingestible supplement to the client computer system as a proposed formula, and inviting modification of same by the client on the client computer system;

receiving modifications to the proposed formula for the supplement at the client computer system, subject to the relational database in the server computer system; and processing the client-requested modifications, if any, to the proposed formula for the supplement at the server computer; then sending the proposed formula for the supplement to the client computer system for approval;

receiving client approval of the proposed formula for the nutritional supplement at the server computer system; and processing the approved proposed formula for the nutritional supplement at the server computer system according to the relational database, and producing the formula as the unique ingestible nutritional supplement for the client.

2. The method of claim 1, wherein the network is a network operating according to a hypertext transfer protocol (HTTP), and wherein the plurality of first statements are a plurality of first questions.

3. The method of claim 2, further comprising:

receiving a plurality of second statements inviting a plurality of second responses at the client computer system;

receiving the plurality of second responses at the server computer system coupled over the network to the client computer system; and processing the plurality of second responses at the server computer system including an additional invitation for an additional response to supply data into the relational database to produce the formula for the unique ingestible nutritional supplement.

4. The method of claim 2 wherein the network is at least one of an Internet and an intranet.

5. In a method for formulating a unique ingestible nutritional supplement through a network operating according to a hypertext transfer protocol (HTTP) in accordance with claim 2, the method comprising the operations of:

receiving a plurality of first statements inviting a plurality of first responses at a client computer system;

receiving the plurality of first responses at the client computer system; receiving the plurality of first responses at a server computer system coupled over the network to the client computer system; and processing the plurality of first responses at the server computer including an additional invitation for an additional response to supply data into a relational database to produce the unique ingestible nutritional supplement from the formula, wherein the supplement is contained in at least one capsule comprising a plurality of ingredients, each of which is present in a quantity according to the supplement formula.

6. The method of claim 1, wherein during the operation of processing the plurality of responses at the server computer system and the operation of returning the formula to the client computer system, the method further comprising:

receiving advertising information at the client computer system.

7. The method of claim 1, further comprising:

receiving an order form at the client computer system inviting at least one response;

receiving the order form having at least one response at the server computer system; and distributing the unique ingestible nutritional supplement as directed on the order form.

8. The method of claim 1, wherein a user of the client computer system is an unrestricted public member, and wherein the relational database maintains a relationship between ingredients in the ingestible formula after modification of the proposed supplement formulation.

9. A server computer system for formulating through a network, a unique ingestible nutritional supplement, not a model, for a client, the server computer system comprising:

a processor;

a network interface coupled to the network and coupled to the processor, the network interface receiving from a remotely located client computer system a plurality of responses to a plurality of statements at the client computer system; and a file storage device coupled to the processor, wherein the file storage device stores (i) copies of the plurality of responses under control of a file management system and (ii) a relational database that maintains relations between ingredients that are available in the unique adjustable formula, and wherein the processor automatically generates the formula for the unique ingestible nutritional supplement from the plurality of responses.

10. The server computer system of claim 9, wherein the network is a network operating according to a hypertext transfer protocol (HTTP).

11. A computer readable storage medium containing executable computer program instructions, which when executed cause a client computer system and a server computer system to perform a method comprising:

receiving a plurality of statements inviting a plurality of responses at a client computer system;

receiving the plurality of responses at the client computer system;

sending the plurality of responses to a server computer system coupled over the network to the client computer system; and processing the plurality of responses at the server computer system including an additional invitation for an additional response to supply data into a relational database to produce a unique ingestible nutritional supplement according to a personalized formula, which is not based upon a model.

12. A distributed readable storage medium containing executable computer program instructions, which when executed cause a client computer system and a server computer system to perform a method for formulating through a network a unique ingestible nutritional supplement, not a model, for a client, the medium comprising:

receiving a plurality of first statements inviting a plurality of responses at a client computer system;

receiving the plurality of responses at the client computer system; sending the plurality of responses to a server computer system coupled over the network to the client computer system; and processing the plurality of responses at the server computer system including an additional invitation for an additional response to supply data into a relational database to produce the formula for the ingestible supplement;

customizing the unique formula to the individual client by repeating the following steps as often as needed to meet the client's needs, comprising:

returning the formula for the ingestible supplement to the client computer system as a proposed formula, and inviting modification of same by the client on the client computer system;

receiving modifications to the proposed formula for the supplement at the client computer system, subject to the relational database in the server computer system;

processing the client-requested modifications, if any, to the proposed formula for the supplement at the server computer; then sending the proposed formula for the supplement to the client computer system for approval;

receiving client approval of the proposed formula for the nutritional supplement at the server computer system; and processing the approved proposed formula for the nutritional supplement at the server computer system according to the relational database, and producing the formula as the unique ingestible nutritional supplement for the client.

13. The distributed readable storage medium of claim 12, wherein the plurality of first statements are a plurality of first questions, and wherein each question invites a yes response or a no response.

14. The distributed readable storage medium of claim 13, the medium further comprising:

receiving a plurality of second statements inviting a plurality of second responses at a client computer system;

receiving the plurality of second responses at a server computer system coupled over the network to the client computer system; and processing the plurality of second responses at the server computer system according to a relational database to produce the formula for the unique ingestible nutritional supplement.

15. The distributed readable storage medium of claim 13 wherein the network is at least one of an Internet and an intranet.

16. The distributed readable storage medium of claim 13 wherein a user of the client computer system is an unrestricted public member and wherein the network is a network operating according to a hypertext transfer protocol (HTTP).

17. The distributed readable storage medium of claim 12, wherein during the operation of processing the plurality of responses at the server computer system and the operation of returning the formula to the client computer system, the medium further comprises:

receiving advertising information at the client computer system.

18. The distributed readable storage medium of claim 12, the medium further comprising:

receiving an order form at the client computer system inviting at least one response;

receiving the order form having at least one response at the server computer system; and distributing the unique ingestible nutritional supplement as directed on the order form.

19. A method for formulating a unique ingestible personal supplement, which is not based upon a model, wherein the method comprises:

receiving a plurality of responses;

comparing each response to at least one criteria;

assigning at least one condition keyword to each response that satisfies at least one criteria;

comparing each condition keyword to at least one condition associated with a first formula for the supplement, and to at least one condition associated with a second formula for the supplement; then if the condition associated with the second supplement formula is satisfied by the condition keyword:

selecting the second formula for the supplement as a proposed formula for the personal supplement, otherwise selecting the first formula for the supplement as the proposed formula for the personal supplement; and recharacterizing the proposed formula for the personal supplement as a unique formula for the personal supplement from which the unique ingestible personal supplement is produced.

20. The method of claim 19, wherein the first formula for the supplement and the second formula for the supplement are in a first package, the method further comprising:
   comparing each condition keyword to at least one condition associated with a third formula for the supplement and to at least one condition associated with a fourth formula for the supplement, wherein the third formula for the supplement and the fourth formula for the supplement are in a second package; and
   if the condition associated with the fourth formula for the supplement is satisfied by the condition keyword,
      combining the fourth formula for the supplement with the recharacterized proposed formula for the personal supplement as the unique formula for the personal supplement, otherwise
      combining the third formula for the supplement with the recharacterized proposed personal formula for the supplement as the unique personal formula for the supplement from which the unique ingestible personal supplement is produced.

21. A method of creating a package of nutritional supplements from the personalized formula for the supplement derived in accordance with the method of claim 19, from an array of pre-mixed nutritional components, the method comprising:
   selecting a first nutritional component having a pre-mixed formulation of at least a first ingredient in a first amount and a second ingredient in a second amount;
   selecting a second nutritional component having a pre-mixed formulation of at least the first ingredient in a third amount and a third ingredient in a fourth amount; and
   assembling the first nutritional component and the second nutritional component into at least one package.

22. The method of claim 21 wherein the second nutritional component comprises the second ingredient in a fifth amount and wherein the first and the second nutritional components are intended to be consumed together to provide the sum of the first amount and the third amount of the first ingredient and to provide the sum of the second amount and the fifth amount of the second ingredient upon ingestion.

23. A method as in claim 21, wherein the array of pre-mixed nutritional components is assembled to provide substantially all of the possible nutritional supplement formulations used by a majority of the possible people who may consume a package of nutritional supplements, and wherein the package is assembled after a client responds to health related questions to create a personalized formula for the unique ingestible nutritional supplement.

* * * * *

UNITED STATES PATENT AND TRADEMARK OFFICE
CERTIFICATE OF CORRECTION

PATENT NO.   : 6,510,430 B1                                                            Page 1 of 1
DATED        : January 21, 2003
INVENTOR(S)  : Bradford S. Oberwager et al.

It is certified that error appears in the above-identified patent and that said Letters Patent is hereby corrected as shown below:

<u>Title page,</u>
Item [75], "Moguin" should read -- Moquin --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,510,430 B2 | Page 1 of 1 |
| APPLICATION NO. | : 09/256946 | |
| DATED | : January 21, 2003 | |
| INVENTOR(S) | : Oberwager et al. | |

It is certified that error appears in the above-identified patent and that said Letters Patent is hereby corrected as shown below:

In column 20, at line 64, delete "for a client, the server computer system comprising:" and insert --for a client, performing the method as disclosed in claim 1, the server computer system comprising:--.

In column 21, at line 19, delete "a server computer system to perform a method comprising:" and insert --a server computer system to perform the method as disclosed in claim 1, comprising:--.

Signed and Sealed this

Twenty-second Day of May, 2007

JON W. DUDAS
*Director of the United States Patent and Trademark Office*